US 6,582,423 B1

(12) United States Patent
Thapliyal et al.

(10) Patent No.: US 6,582,423 B1
(45) Date of Patent: Jun. 24, 2003

(54) ELECTROSURGICAL SYSTEMS AND METHODS FOR RECANALIZATION OF OCCLUDED BODY LUMENS

(75) Inventors: Hira V. Thapliyal, Los Altos, CA (US); Philip E. Eggers, Dublin, OH (US)

(73) Assignee: Arthrocare Corporation, Sunnyvale, CA (US)

(*) Notice: Subject to any disclaimer, the term of this patent is extended or adjusted under 35 U.S.C. 154(b) by 0 days.

(21) Appl. No.: 09/062,869

(22) Filed: Apr. 20, 1998

Related U.S. Application Data

(63) Continuation-in-part of application No. 08/874,173, filed on Jun. 13, 1997, now Pat. No. 6,179,824.

(51) Int. Cl.[7] ............................................. A61B 18/14
(52) U.S. Cl. ...................... 606/32; 606/41; 128/898; 607/99; 607/105; 607/113; 604/114
(58) Field of Search ...................... 606/41, 32; 607/99, 607/105, 113; 604/35, 114; 128/898

(56) References Cited

U.S. PATENT DOCUMENTS

| 2,050,904 | A | 8/1936 | Trice | 128/303 |
|---|---|---|---|---|
| 4,033,351 | A | 7/1977 | Hetzel | 128/305 |
| 4,040,426 | A | 8/1977 | Morrison, Jr. | 128/303 |
| 4,043,342 | A | 8/1977 | Morrison, Jr. | 128/303 |
| 4,116,198 | A | 9/1978 | Roos | 128/303 |
| 4,202,337 | A | 5/1980 | Hren et al. | 128/303 |
| 4,228,800 | A | 10/1980 | Degler, Jr. et al. | 128/303 |

(List continued on next page.)

FOREIGN PATENT DOCUMENTS

| EP | 0703461 | 3/1996 | G01R/27/02 |
|---|---|---|---|
| EP | 0740926 | 11/1996 | A61B/17/39 |

(List continued on next page.)

OTHER PUBLICATIONS

E. Kramolowsky et al. (1991) *J. of Urology* 146:669–674.
R. Tucker et al. (1990) *Urol. Res.* 18:291–294.
R. Tucker et al. (1989) *J. of Urology* 141:662–665.
R. Tucker et al. (1989) Abstract P14–11, 7th World Congress on Endourology and ESWL, Nov. 27–30, 1989, Kyoto, Japan.
C. Slager et al. (1987) *Z. Kardiologie* 76(6):67–71.
C. Slager et al. (1995) *JACC* 5(6):1382–6.
P. Nardella (1989) *SPIE* 1068:42–49.
Elsasser et al. (1976) *Medizinal–Markt/Acta Medicotechnica* 24(4):129–134.

*Primary Examiner*—Lee Cohen

(57) ABSTRACT

The present invention comprises electrosurgical apparatus and methods for maintaining patency in body passages subject to occlusion by invasive tissue growth. The apparatus and methods of the present invention may be used to open and maintain patency in virtually any hollow body passage which may be subject to occlusion by invasive cellular growth or invasive solid tumor growth. Suitable hollow body passages include ducts, orifices, lumens, and the like, with exemplary body passages including the coronary arteries. The present invention is particularly useful for reducing or eliminating the effects of restenosis in coronary arteries by selectively removing tissue ingrowth in or around stents anchored therein.

51 Claims, 30 Drawing Sheets

U.S. PATENT DOCUMENTS

| | | | |
|---|---|---|---|
| 4,232,676 A | 11/1980 | Herczog | 128/303 |
| 4,248,231 A | 2/1981 | Herczog et al. | 128/303 |
| 4,326,529 A | 4/1982 | Doss et al. | 128/303 |
| 4,381,007 A | 4/1983 | Doss | 128/303 |
| 4,476,862 A | 10/1984 | Pao | 128/303 |
| 4,532,924 A | 8/1985 | Auth et al. | 128/303 |
| 4,548,207 A | 10/1985 | Reimels | 128/303 |
| 4,567,890 A | 2/1986 | Ohta et al. | 128/303 |
| 4,582,057 A | 4/1986 | Auth et al. | 128/303 |
| 4,643,186 A | 2/1987 | Rosen et al. | 128/303 |
| 4,646,737 A | 3/1987 | Hussein et al. | 128/303 |
| 4,654,024 A | 3/1987 | Crittendon et al. | 604/49 |
| 4,672,962 A | 6/1987 | Hershenson | 128/303 |
| 4,674,499 A | 6/1987 | Pao | 128/303 |
| 4,682,596 A | 7/1987 | Bales et al. | 604/22 |
| 4,706,667 A | 11/1987 | Roos | 128/303 |
| 4,709,698 A | 12/1987 | Johnston et al. | 128/303 |
| 4,765,331 A | 8/1988 | Petruzzi et al. | 128/303 |
| 4,799,479 A | 1/1989 | Spears | 128/303 |
| 4,823,791 A | 4/1989 | D'Amelio | 123/303 |
| 4,860,743 A | 8/1989 | Abela | 128/303 |
| 4,860,752 A | 8/1989 | Turner | 128/422 |
| 4,907,586 A | 3/1990 | Bille et al. | 606/5 |
| 4,955,377 A | 9/1990 | Lennox et al. | 128/401 |
| 4,967,765 A | 11/1990 | Turner et al. | 128/785 |
| 4,976,709 A | 12/1990 | Sand | 606/5 |
| 4,976,711 A | 12/1990 | Parins et al. | 606/48 |
| 4,998,933 A | 3/1991 | Eggers et al. | 606/41 |
| 5,000,751 A | 3/1991 | Schroder et al. | 606/4 |
| 5,007,908 A | 4/1991 | Rydell | 606/47 |
| 5,009,656 A | 4/1991 | Reimels | 128/303 |
| 5,035,696 A | 7/1991 | Rydell | 606/47 |
| 5,041,109 A | 8/1991 | Abela | 606/15 |
| 5,057,105 A | 10/1991 | Malone et al. | 606/28 |
| 5,057,106 A | 10/1991 | Kasevich et al. | 606/33 |
| 5,078,717 A | 1/1992 | Parins et al. | 606/48 |
| 5,078,736 A | 1/1992 | Behl | 623/1 |
| 5,083,565 A | 1/1992 | Parins | 128/642 |
| 5,098,431 A | 3/1992 | Rydell | 606/48 |
| 5,108,391 A | 4/1992 | Flachenecker et al. | 606/38 |
| 5,122,138 A | 6/1992 | Manwaring | 606/46 |
| 5,125,928 A | 6/1992 | Parins et al. | 606/48 |
| 5,137,530 A | 8/1992 | Sand | 606/5 |
| 5,140,987 A | 8/1992 | Schuger et al. | 128/642 |
| 5,152,759 A | 10/1992 | Parel et al. | 606/5 |
| 5,178,618 A | 1/1993 | Kandarpa | 606/28 |
| 5,178,620 A | 1/1993 | Eggers et al. | 606/41 |
| 5,190,517 A | 3/1993 | Zieve et al. | 604/22 |
| 5,190,540 A | 3/1993 | Lee | 606/28 |
| 5,195,959 A | 3/1993 | Smith | 604/34 |
| 5,197,963 A | 3/1993 | Parins | 606/46 |
| 5,217,457 A | 6/1993 | Delahuerga et al. | 606/42 |
| 5,222,938 A | 6/1993 | Behl | 604/49 |
| 5,224,953 A | 7/1993 | Morgentaler | 606/192 |
| 5,230,334 A | 7/1993 | Klopotek | 128/399 |
| 5,246,438 A | 9/1993 | Langberg | 606/33 |
| 5,250,045 A | 10/1993 | Bohley | 606/7 |
| 5,263,951 A | 11/1993 | Spears et al. | 606/12 |
| 5,267,994 A | 12/1993 | Gentelia et al. | 606/15 |
| 5,267,997 A | 12/1993 | Farin et al. | 606/38 |
| 5,273,524 A | 12/1993 | Fox et al. | 604/21 |
| 5,281,211 A | 1/1994 | Parel et al. | 606/5 |
| 5,281,216 A | 1/1994 | Klicek | 606/42 |
| 5,281,218 A | 1/1994 | Imran | 606/41 |
| 5,290,282 A | 3/1994 | Casscells | 606/29 |
| 5,292,321 A | 3/1994 | Lee | 606/28 |
| 5,300,069 A | 4/1994 | Hunsberger et al. | 606/37 |
| 5,312,400 A | 5/1994 | Bales et al. | 606/41 |
| 5,314,406 A | 5/1994 | Arias et al. | 604/21 |
| 5,330,470 A | 7/1994 | Hagen | 606/42 |
| 5,334,190 A | 8/1994 | Seiler | 606/5 |
| 5,342,357 A | 8/1994 | Nardella | 606/40 |
| 5,348,553 A | 9/1994 | Whitney | 606/41 |
| 5,366,443 A | 11/1994 | Eggers et al. | 604/114 |
| 5,370,675 A | 12/1994 | Edwards et al. | 607/101 |
| 5,374,265 A | 12/1994 | Sand | 606/5 |
| 5,380,277 A | 1/1995 | Philips | 604/33 |
| 5,380,316 A | 1/1995 | Aita et al. | 606/7 |
| 5,383,917 A | 1/1995 | Desai et al. | 607/702 |
| 5,389,096 A | 2/1995 | Aita et al. | 606/15 |
| 5,395,312 A | 3/1995 | Desai | 604/22 |
| 5,400,428 A | 3/1995 | Grace | 385/115 |
| 5,417,687 A | 5/1995 | Nardella et al. | 606/32 |
| 5,419,767 A | 5/1995 | Eggers et al. | 604/114 |
| 5,423,806 A | 6/1995 | Dale | 606/15 |
| 5,423,882 A | 6/1995 | Jackman et al. | 607/122 |
| 5,425,355 A | 6/1995 | Kulick | 128/4 |
| 5,429,604 A | 7/1995 | Hammersmark et al. | 604/95 |
| 5,433,708 A | 7/1995 | Nichols et al. | 604/113 |
| 5,437,658 A | 8/1995 | Muller et al. | 606/5 |
| 5,441,499 A | 8/1995 | Fritzsch | 606/45 |
| 5,454,809 A | 10/1995 | Janssen | 606/41 |
| 5,456,680 A | 10/1995 | Taylor | 606/2 |
| 5,484,433 A | 1/1996 | Taylor | 606/17 |
| 5,500,012 A | 3/1996 | Brucker et al. | 607/122 |
| 5,505,725 A | 4/1996 | Samson | 606/7 |
| 5,507,771 A | 4/1996 | Gianturco | 606/198 |
| 5,514,128 A | 5/1996 | Hillsman et al. | 606/7 |
| 5,514,130 A | 5/1996 | Baker | 606/41 |
| 5,540,712 A | 7/1996 | Kleshinski et al. | 606/198 |
| 5,542,928 A | 8/1996 | Evans et al. | 604/113 |
| 5,545,161 A | 8/1996 | Imran | 606/41 |
| 5,545,211 A | 8/1996 | An et al. | 623/1 |
| 5,554,152 A | 9/1996 | Aita et al. | 606/7 |
| 5,569,242 A | 10/1996 | Lax et al. | 606/42 |
| 5,571,169 A | 11/1996 | Plaia et al. | 623/1 |
| 5,579,764 A | 12/1996 | Goldreyer | 607/122 |
| 5,584,872 A | 12/1996 | LaFontaine et al. | 607/116 |
| 5,603,731 A | 2/1997 | Whitney | 607/121 |
| 5,609,151 A | 3/1997 | Mulier et al. | 128/642 |
| 5,620,438 A | 4/1997 | Amplatz et al. | 606/10 |
| 5,643,251 A | 7/1997 | Hillsman et al. | 606/7 |
| 5,643,255 A | 7/1997 | Organ | 606/41 |
| 5,647,869 A | 7/1997 | Goble | 606/37 |
| 5,673,695 A | 10/1997 | McGee et al. | 128/642 |
| 5,676,693 A | 10/1997 | LaFontaine | 601/116 |
| 5,681,282 A | 10/1997 | Eggers et al. | 604/114 |
| 5,683,366 A | 11/1997 | Eggers et al. | 604/114 |
| 5,697,281 A | 12/1997 | Eggers et al. | 604/114 |
| 5,697,536 A | 12/1997 | Eggers et al. | 604/114 |
| 5,697,882 A | 12/1997 | Eggers et al. | 604/114 |
| 5,697,909 A | 12/1997 | Eggers et al. | 604/114 |
| 5,700,262 A | 12/1997 | Acosta | 606/48 |
| 5,725,524 A | 3/1998 | Mulier et al. | 606/41 |
| 5,749,914 A | 5/1998 | Janssen | 607/116 |
| 5,766,153 A | 6/1998 | Eggers et al. | 604/114 |
| 5,766,192 A | 6/1998 | Zacca | 606/159 |
| 5,775,338 A | 7/1998 | Hastings | 128/898 |
| 5,807,395 A | 9/1998 | Mulier et al. | 606/41 |
| 5,823,955 A | 10/1998 | Kuck et al. | 600/374 |
| 5,836,868 A | 11/1998 | Resseman et al. | 606/159 |
| 5,860,951 A | 1/1999 | Eggers et al. | 604/49 |
| 5,860,974 A | 1/1999 | Abele | 606/41 |
| 5,873,855 A | 2/1999 | Eggers et al. | 604/114 |
| 5,885,277 A | 3/1999 | Korth | 606/35 |

FOREIGN PATENT DOCUMENTS

| | | | | |
|---|---|---|---|---|
| EP | 0754437 | 1/1997 | | A61B/17/39 |
| GB | 2308979 | 7/1997 | | A61B/17/39 |
| GB | 2308980 | 7/1997 | | A61B/17/36 |

| | | | | | | | |
|---|---|---|---|---|---|---|---|
| GB | 2308981 | 7/1997 | ........... A61B/17/39 | WO | 95/34259 | 12/1995 | ............. A61F/5/48 |
| GB | 2327350 | 1/1999 | ........... A61B/17/39 | WO | 96/35469 | 11/1996 | ........... A61M/25/00 |
| GB | 2327351 | 1/1999 | ........... A61B/17/39 | WO | 96/39962 | 12/1996 | ........... A61B/17/36 |
| GB | 2327352 | 1/1999 | ........... A61B/17/39 | WO | 96/39964 | 12/1996 | ........... A61B/17/36 |
| JP | 57-117843 | 7/1982 | ........... A61B/17/39 | WO | 96/39965 | 12/1996 | ........... A61B/17/36 |
| WO | WO 90/07303 | 7/1990 | ........... A61B/17/39 | WO | 97/00646 | 1/1997 | ........... A61B/17/39 |
| WO | WO 92/21278 | 12/1992 | ............ A61B/5/04 | WO | 97/00647 | 1/1997 | ........... A61B/17/39 |
| WO | 93/20747 | 10/1993 | ............ A61B/5/00 | WO | 97/24073 | 7/1997 | ........... A61B/17/39 |
| WO | 94/03134 | 2/1994 | ............. A61F/9/00 | WO | 97/24993 | 7/1997 | ........... A61B/17/39 |
| WO | 94/26228 | 11/1994 | .......... A61G/17/36 | WO | 97/24994 | 7/1997 | ........... A61B/17/39 |
| WO | 95/05780 | 3/1995 | | WO | 97/48346 | 12/1997 | ........... A61B/17/39 |

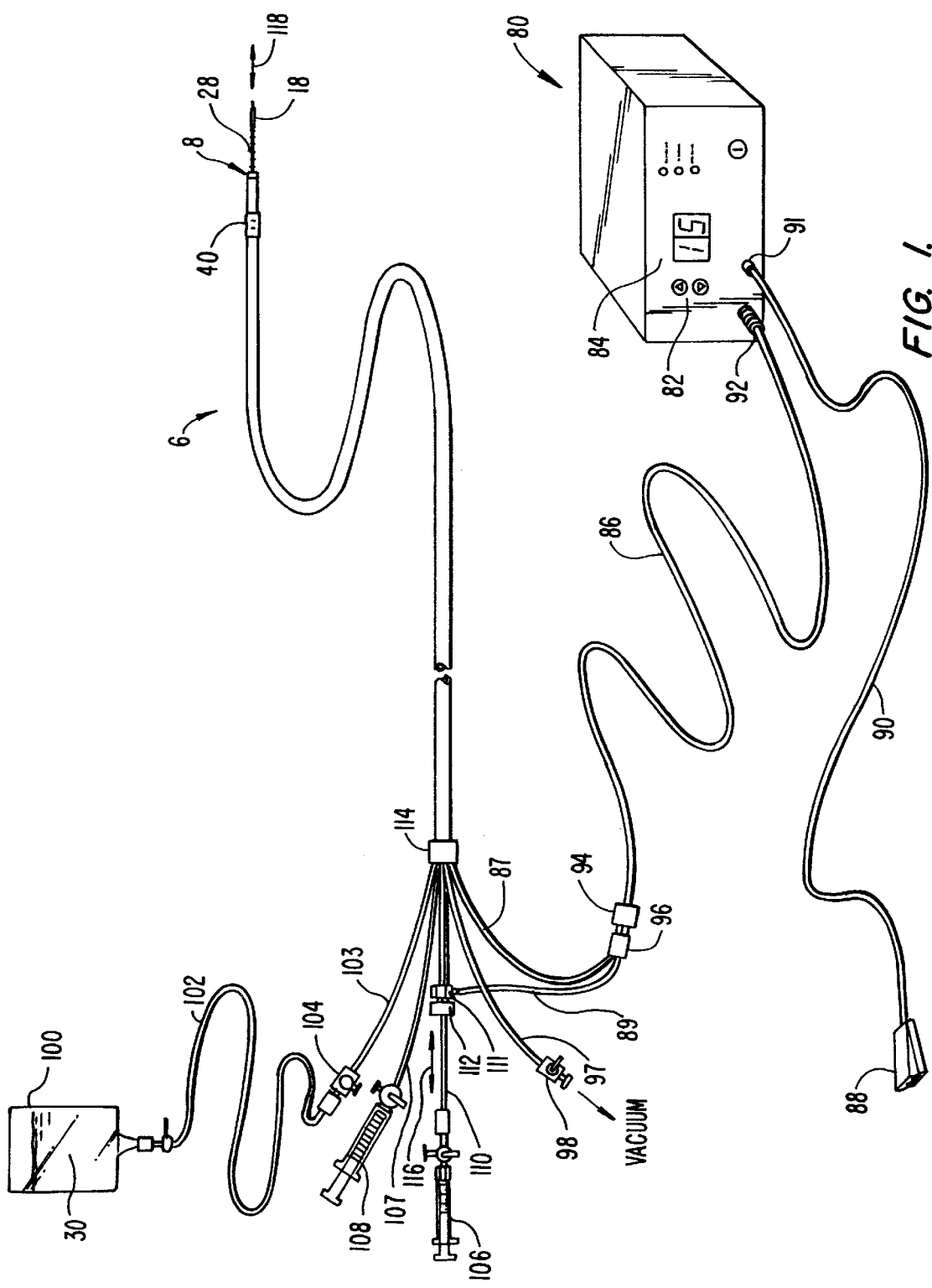

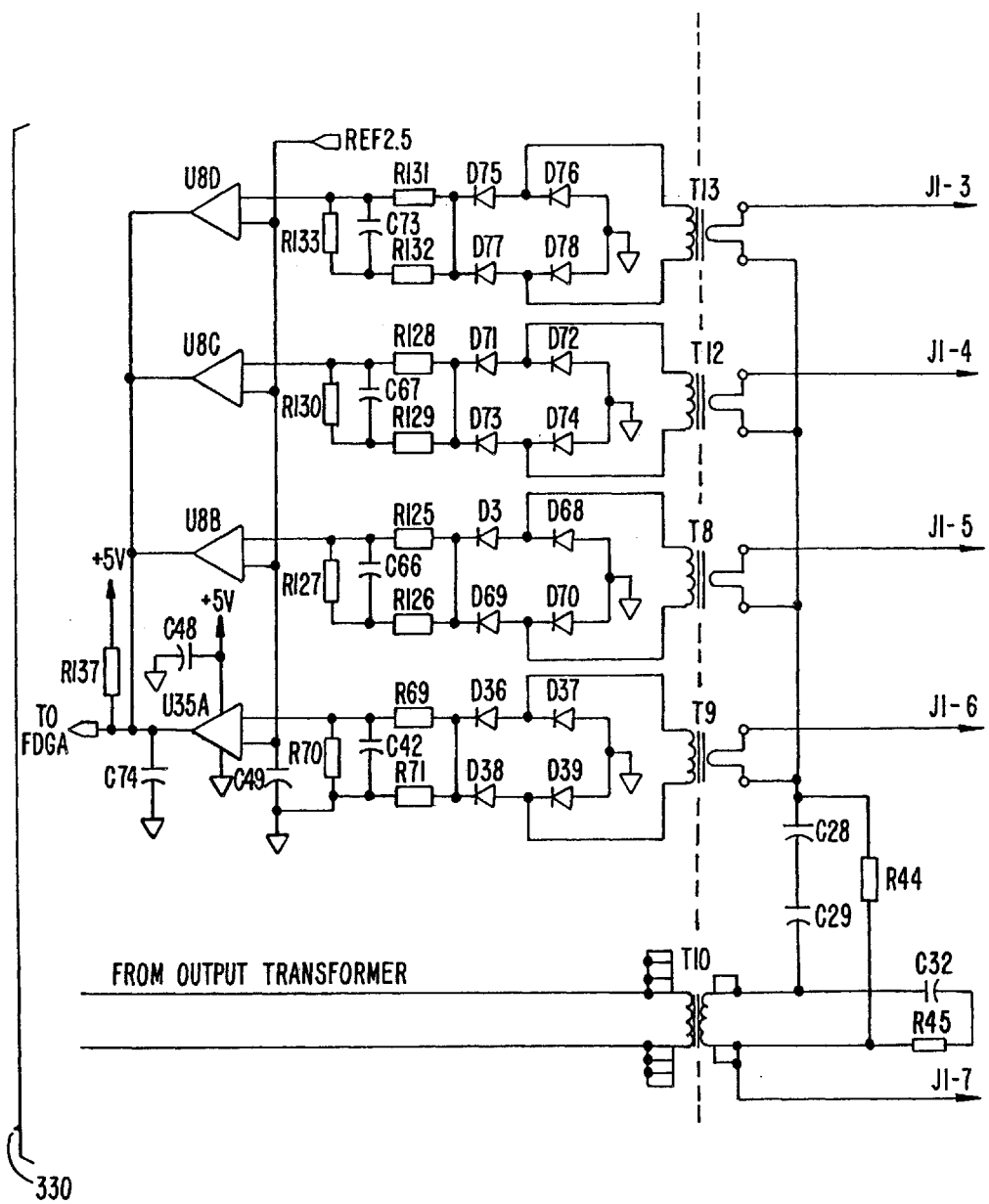
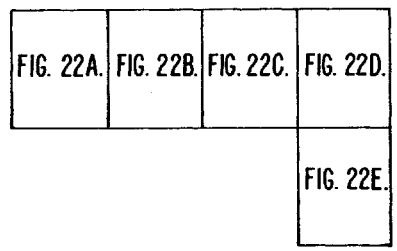
FIG. 22E.
FIG. 22.

ELECTROSURGICAL SYSTEMS AND METHODS FOR RECANALIZATION OF OCCLUDED BODY LUMENS

CROSS-REFERENCE TO RELATED APPLICATIONS

The present application is a continuation-in-part of U.S. application Ser. No. 08/874,173, filed Jun. 13, 1997, now U.S. Pat No. 6,179,824 and this application derives priority from U.S. application Ser. No. 09/002,315, filed Jan. 2, 1998, now U.S. Pat. No. 6,183,469, the complete disclosures of which are incorporated herein by reference for all purposes.

The present invention is related to commonly assigned co-pending U.S. patent application Ser. No. 08/990,374, filed Dec. 15, 1997, which is a continuation-in-part of U.S. patent application Ser. No. 08/485,219, filed on Jun. 7, 1995, now U.S. Pat. No. 5,697,281, Provisional Patent Application No. 60/075,059, filed on Feb. 18, 1998, U.S. patent application No. Ser. No. 09/010,382, filed Jan. 21, 1998, and U.S. patent application Ser. No. 09/032,375, filed Feb. 27, 1998, U.S. patent application Ser. No. 08/977,845, filed on Nov. 25, 1997, Ser. No. 08/942,580, filed on Oct. 2, 1997, Ser. No. 09/026,851, filed Feb. 20, 1998, U.S. application Ser. No. 08/753,227, filed on Nov. 22, 1996, U.S. application Ser. No. 08/687792, filed on Jul. 18, 1996, and PCT International Application, U.S. National Phase Serial No. PCT/US94/05168, filed on May 10, 1994, now U.S. Pat. No. 5,697,909, which was a continuation-in-part of U.S. patent application Ser. No. 08/059,681, filed on May 10, 1993, which was a continuation-in-part of U.S. patent application Ser. No. 07/958,977, filed on Oct. 9, 1992 which was a continuation-in-part of U.S. patent application No. 07/817,575, filed on Jan. 7, 1992, the complete disclosures of which are incorporated herein by reference for all purposes. The present invention is also related to commonly assigned U.S. Pat. No. 5,683,366, filed Nov. 22, 1995, the complete disclosure of which is incorporated herein by reference for all purposes.

BACKGROUND OF THE INVENTION

The present invention relates generally to apparatus and methods for maintaining patency in body passages and more particularly to a catheter system capable of selectively ablating occlusive media within a body lumen. The present invention is particularly useful for the electrosurgical cutting or ablation of invasive tissue growth in and around a stent anchored in the body lumen to help reduce or eliminate restenosis of the body lumen.

When a patient is suffering from atherosclerosis, significant occlusions or blockages are formed on the interior wall of the artery. As a result of these occlusions, the organ or extremity to which blood is to be supplied is compromised and the patient may experience a myocardial infarction or stroke. In less severe cases, it is often sufficient to treat the symptoms with pharmaceuticals and lifestyle modification to lessen the underlying causes of the disease. In more severe cases, a coronary artery blockage can often be treated using endovascular techniques such as balloon angioplasty, atherectomy, laser or hot tip ablation, placement of stents, and the like.

Percutaneous transluminal balloon angioplasty (PTBA) has become a recognized method of reducing the occlusion of blood vessels. The procedure involves routing a catheter having an inflatable balloon at the distal end thereof through the vascular system until the balloon is positioned at the site of the stenotic lesion to be treated. The balloon is then inflated to compress the atherosclerotic plaque into the wall of the blood vessel, thus increasing the size of the opening and enhancing blood flow through the affected artery. However, this successful procedure is overshadowed by the occurrence of restenosis, a re-narrowing of the artery. Studies have shown that 30–40 percent of angioplasty patients experience restenosis within 3–6 months of the angioplasty procedure. When restenosis occurs, patients may be treated with cardiovascular medications, additional angioplasty procedures or bypass surgery.

Restenosis often occurs because the wall of the dilated artery tends to spring back to its original shape following deflation of the dilation balloon. Arterial stenting has been introduced as a solution to the recoil of the vessel wall. Arterial stenting involves the placement of an expandable coil spring or wire-mesh tube within the occluded artery to reopen the lumen of the blood vessel. One example of an arterial stent is disclosed in U.S. Pat. No. 4,739,792 to Julio Palmaz. The Palmaz device comprises an expandable wire-mesh graft or prosthesis which is mounted upon an inflatable balloon catheter. The catheter assembly, including the graft, is delivered to the occluded area and is then inflated to radially force the graft into contact with the occlusion. As the graft expands, the lumen of the blood vessel is opened and blood flow is restored. After complete expansion of the graft, the balloon catheter is deflated and removed, leaving behind the graft to buttress and prevent elastic recoil of the blood vessel wall.

Although this method is successful in preventing recoil of the vessel wall, restenosis will often still occur. Smooth muscle cells which form the vessel wall tend to proliferate and build-up in the newly stented area of the blood vessel. This cellular buildup may eventually become large enough to block the lumen of the blood vessel.

It has recently been determined that localized heating of the blood vessel wall may inhibit the proliferation of smooth muscle cells which are believed to cause restenosis. One example of localized blood vessel heating is disclosed in U.S. Pat. No. 4,799,479 to Spears. The Spears patent discloses an apparatus for angioplasty having an inflatable balloon catheter which is provided with a meshwork of electrical wires to supply heat to a vessel wall. Following balloon angioplasty, the external surface of the balloon is heated to fuse together disrupted tissue elements and to kill smooth muscle cells which are believed to lead to restenosis. Unfortunately, the Spears device does not adequately prevent the spontaneous elastic recoil of the arterial wall. Immediately following angioplasty, the arterial wall begins to spring back to its original shape.

Thus stenting in and of itself is ineffective in preventing restenosis due to the occurrence of cellular proliferation. Likewise, balloon dilation in combination with localized heating does not adequately prevent restenosis since the vessel wall tends to spontaneously return to its original occluded shape.

Other techniques have recently been developed to help reduce incidences of restenosis. For example, procedures for irradiating the angioplasty site with UV light to reduce the proliferation of smooth muscle cells at the site have been disclosed. In addition, techniques have been disclosed for the controlled application of thermal and/or electrical energy directly to the stent by, for example, including resistive or inductive heating elements that may include radiofrequency electrodes within the stent. The radiofrequency energy is then applied to the stent to disrupt the cellular growth in or around the stent. One major disadvantage of these procedures is that it is difficult to selectively apply the energy to the invasive tissue without causing thermal damage to the body lumen wall. In particular, methods that apply energy, such as RF energy, directly to the stent will often cause thermal damage to the surrounding body lumen in which the stent is anchored.

SUMMARY OF THE INVENTION

The present invention comprises apparatus and methods for maintaining patency in body passages subject to occlusion by invasive tissue growth. The apparatus and methods of the present invention may be used to open and maintain patency in virtually any hollow body passage which may be subject to occlusion by invasive cellular growth or invasive solid tumor growth. Suitable hollow body passages include ducts, orifices, lumens, and the like, with exemplary body passages including the coronary arteries. The present invention is particularly useful for reducing or eliminating the effects of restenosis in coronary arteries by selectively removing tissue ingrowth in or around stents anchored therein.

The principles of the present invention are generally applicable to any body lumen which becomes partially or totally occluded. Methods of the present invention comprise advancing an electrosurgical catheter within the body passage such that an electrode terminal is positioned near the occlusive media. High frequency voltage is applied to one or more electrode terminal(s) at the distal end of the catheter such that an electrical current flows from the electrode terminal(s), through the region of the occlusive media, and to a return electrode to volumetrically remove the occlusive media in situ. In exemplary embodiments, the high frequency voltage is sufficient to effect molecular dissociation or disintegration of the occlusive media, thus converting the solid media into non-condensable gases.

The present invention is particularly useful in a lumen containing a lumenal prosthesis, such as a stent, stent-graft or graft, which may be metallic, non-metallic or a non-metallic coated metallic structure. Restenosis often occurs when arthermateous media or thrombus moves or grows through or around the cylindrical wall of the prosthesis to partially occlude the body passage. Methods of the present invention comprise advancing an electrosurgical catheter within the body passage such that an electrode terminal is positioned near the occlusive media. High frequency voltage is applied to one or more electrode terminal(s) at the distal end of the catheter such that an electrical current flows from the electrode terminal(s), through the region of the occlusive media, and to a return electrode to selectively remove the occlusive media without directly applying thermal or electrical energy to the prosthesis or the lumenal wall. The electrode terminal may then be advanced through the vacancy left by the removed occlusive media to recanalize the vessel. By selectively removing the occlusive media without passing energy directly to the stent, thermal damage to the surrounding lumenal wall is minimized.

In an exemplary embodiment, the return electrode is located on the catheter so that the current flow paths are confined between the return electrode and one or more electrode terminals in the vicinity of the working end of the catheter. This confinement of current flow paths minimizes the undesired flow of current through portions or all of the stent, which may otherwise induce non-specific tissue injury beyond the site of recanalization of the occluded lumen. In one configuration, the return electrode is a movable guide wire positioned radially inward from the electrode terminal such that the electrical current flows from the electrode terminal radially inward to the return electrode, thereby inhibiting current flow through the prosthesis. In another embodiment, the return electrode is an annular band positioned proximal of the electrode terminal(s).

In preferred embodiments, the high frequency voltage is applied in the presence of electrically conducting fluid such that a current flow path is generated between the electrode terminal(s) and the return electrode through the electrically conducting fluid. Preferably, the electrically conductive fluid is delivered through an internal lumen in the catheter (or through a separate instrument) to a region around the occlusive media to displace naturally occurring bodily fluids. This region may be fluidly isolated to confine the electrically conducting fluid around the tissue ablation site. In one embodiment, the region is isolated by advancing proximal and distal balloons to either side of the region, and inflating these balloons to effect a seal with the interior wall of the body passage.

Once the target site is isolated from the rest of the vasculature, the supply of electrically conductive fluid is continuously delivered to the region and balanced with the aspiration of fluid from the site of intended recanalization. The electrode terminal(s) are energized by applying a high frequency voltage between electrode terminal(s) and the return electrode, which can be a movable guide wire. A high electric field is created at the surface of the electrode(s) which causes the volumetric removal or ablation of target tissue in close proximity with the electrode terminal(s). As the occlusive media is ablated, gaseous products are generated which are entrained in the electrically conducting fluid and removed through the aspiration lumen in the catheter. The current flux lines are generally confined to the central portion of tissue ablation region because they generally flow inward towards the return electrode and because the occlusive media generally shields the outer region of the body passage (including the stent) from the current flux lines. This minimizes undesirable interaction between the electrical current and the stent. In an exemplary embodiment, the distal portion of the catheter body is reciprocally rotated as the electrode terminal is energized to selectively ablate the occlusive media. The catheter body is then advanced through the vacancy left by the ablated occlusive media to recanalize the vessel.

In a specific configuration, the occlusive media is removed by molecular dissociation or disintegration processes. In these embodiments, the high frequency voltage applied to the electrode terminal(s) is sufficient to vaporize an electrically conductive fluid (e.g., saline or blood) between the electrode terminal(s) and the occlusive media. Within the vaporized fluid, a ionized plasma is formed and charged particles (e.g., electrons) are accelerated towards the target media to cause the molecular breakdown or disintegration of several cell layers of the media. This molecular dissociation is accompanied by the volumetric removal of the media. The short range of the accelerated charged particles within the plasma layer confines the molecular dissociation process to the surface layer to minimize damage and necrosis to the surrounding blood vessel walls. This process can be precisely controlled to effect the volumetric removal of tissue or media as thin as 10 to 150 microns with minimal heating of, or damage to, surrounding or underlying tissue structures. A more complete description of this phenomena is described in commonly assigned U.S. Pat. No. 5,683,366, the complete disclosure of which is incorporated herein by reference.

Apparatus of the present invention comprise a catheter shaft having a flexible body with a proximal end portion and a distal end portion with one or more electrode terminal(s), and a connector extending through the body for coupling the electrode terminal(s) to a source of high frequency voltage. Upon the application of sufficient high frequency voltage to the electrode terminal(s), the occlusive media is volumetrically removed from the body lumen to recanalize the body lumen. In some embodiments, the apparatus will further include one or more fluid delivery element(s) for delivering electrically conducting fluid to the electrode terminal(s) and the target site. The fluid delivery element(s) may be located on the catheter, e.g., one or more fluid lumen(s) or tube(s), or they may be part of a separate instrument. In an exemplary embodiment, the electrically conducting fluid will preferably generate a current flow path between the electrode terminal(s) and one or more return electrode(s). In an exemplary embodiment, the return electrode(s) are located on the catheter and spaced a sufficient distance from the electrode terminal(s) to substantially avoid or minimize current shorting therebetween and to shield the return electrode(s) from tissue at the target site. Alternatively, the return electrode(s) may comprise a dispersive pad located on the outer surface of the patient (i.e., a monopolar modality).

In a specific configuration, the apparatus includes a plurality of electrically isolated electrode terminals extending from the distal end of the catheter shaft. The electrode terminals are each mounted within an electrically insulating support member, and spaced peripherally around the distal opening of the catheter body. In these embodiments, the catheter may include a single, annular return electrode located proximal of the distal opening, or a plurality of electrode terminals mounted to the support members proximal of the electrode terminals. In this embodiment, the catheter body also includes one or more fluid delivery lumens spaced peripherally around the central lumen for delivering electrically conductive fluid to the electrode terminals. In addition, the catheter body will preferably include one or more suction lumens spaced peripherally around the central lumen, and suitably coupled to an external suction source for aspirating fluid, tissue and/or gaseous products of ablation (e.g., non-condensable gases) from the target site.

In an exemplary embodiment, the working end portion of the catheter has an adjustable outer diameter to facilitate advancement of this portion of the catheter through a variable diameter body lumen or stent. In one configuration, the working end of the catheter will taper in the distal direction (e.g., in a series of steps) so that the surgeon can advance the catheter through a severely occluded body lumen. The catheter may include a series of axially spaced electrode terminal(s) that are electrically isolated from each other to allow for each set to be independently activated. By way of example, in a severely occluded body lumen, the surgeon may activate the distal set of electrode terminal(s) to remove the innermost occlusive media, advance these distal electrode terminal(s) through the vacancy left by the removed occlusive media, and then activate a more proximal, and radially outward, set of electrode terminal(s) to remove occlusive media radially outward from the initially removed media.

In another configuration, the working end of the catheter may be radially expandable and compressible so that the diameter of the working end can be varied as the catheter is advanced through the lumen. In some instances, stents will not expand uniformly resulting in portions of the stent having smaller inner diameters. In other instances, vessel wall pressure may cause portions of the stent to spring back to its original shape or partially back to this shape so that the overall inner diameter of the stent varies in the axial direction. Accordingly, the present invention allows the diameter of the working end of the catheter to vary (either automatically in response to the body lumen or stent inner diameter, or through activation by the surgical team) to facilitate advancement through non-uniform stents or body lumens.

In another embodiment of the invention, the catheter system includes a high frequency power supply configured to reduce or interrupt power when the electrode terminal(s) contact a low impedance object, such as a stent within the body lumen. In one embodiment, the power supply includes a spark prevention device for eliminating or reducing sudden pulses in current when an instrument powered by the power supply contacts a low impedance source. The spark limiting device is coupled to one or more current sensors on the electrode terminal(s) to substantially continuously monitor current output, interrupting current output from the output driver when current output from the output current sensor exceeds a predetermined threshold level. The spark prevention mechanism, which may be used in conjunction with other power limiting devices, preferably turns off output from the power supply when output current from the supply exceeds a predetermined current level.

BRIEF DESCRIPTION OF THE DRAWINGS

FIG. 1 schematically illustrates a lumen recanalization catheter system according to the present invention;

DESCRIPTION OF SPECIFIC EMBODIMENTS

Figure 2A:
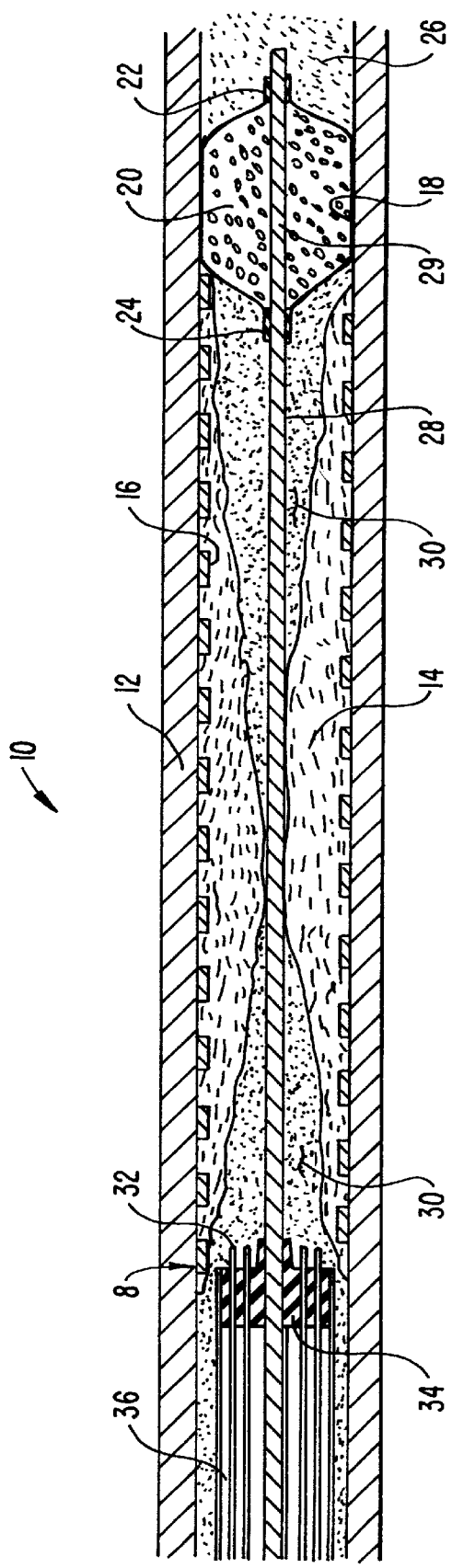
FIGS. 2A–2C illustrate a method of recanalizing an obstructed lumen according to the present invention.

The present invention relates generally to the field of electrosurgery, and more particularly to surgical devices, systems and methods which employ high frequency electrical energy to remove or ablate tissue attached to implanted objects within the body. The systems and methods of the present invention are particularly useful for removing atheromatous material which partially or fully occludes the body lumen, such as a blood vessel or for removing stents or other implanted objects. Moreover, other body lumens that may be treated by the method and apparatus of the present invention include the urinary tract (which for example may be occluded by an enlarged prostrate in males), the fallopian tubes (which may be occluded and cause infertility), and the like. In fact, the methods and apparatus disclosed herein may be used in a wide variety of procedures, including open procedures, intravascular procedures, urology, laparascopy, arthroscopy, thoracoscopy or other cardiac procedures, dermatology, orthopedics, gynecology, otorhinolaryngology, spinal and neurologic procedures, oncology and the like. For convenience, the remaining disclosure will be directed specifically to the removal of occlusive media within body lumens.

The stenotic material in blood vessels will be, by way of example but not limited to, atheroma or atheromatous plaque. It may be relatively soft (fresh) or it may be calcified and hardened. The invention applies heat selectively to the stenotic material to remove this material while limiting unwanted heating of the blood, the surrounding vessel wall and the stent anchored therein. In some embodiments, the present invention confines the current flow paths between the return electrode and electrode terminals to the vicinity of the tissue ablating region. This confinement of current flow paths minimizes the undesired flow of current through the walls of the body passage, or portions or all of the stent, which may otherwise induce non-specific tissue injury beyond the site of recanalization of the occluded lumen.

In the present invention, high frequency (RF) electrical energy is applied to one or more electrode terminals (usually in the presence of electrically conductive fluid) to remove and/or modify body structures. Depending on the specific procedure, the present invention may be used to: (1) volumetrically remove body structures (i.e., ablate or effect molecular dissociation of the structure); (2) cut or resect body structures; (3) vaporize, cauterize or desiccate structures and/or (4) coagulate and seal severed blood vessels.

In the preferred method of the present invention, occlusive media within body lumens is volumetrically removed or ablated. In this procedure, a high frequency voltage difference is applied between one or more electrode terminal(s) and one or more return electrode(s) to develop high electric field intensities in the vicinity of the target tissue. The high electric field intensities lead to electric field induced molecular breakdown of target tissue through molecular dissociation (rather than thermal evaporation or carbonization). Applicant believes that the tissue structure is volumetrically removed through molecular disintegration of larger organic molecules into smaller molecules and/or atoms, such as hydrogen, oxides of carbon, hydrocarbons and nitrogen compounds. This molecular disintegration completely removes the tissue structure, as opposed to dehydrating the tissue material by the removal of liquid within the cells of the tissue, as is typically the case with electrosurgical desiccation and vaporization.

The high electric field intensities may be generated by applying a high frequency voltage that is sufficient to vaporize an electrically conducting fluid over at least a portion of the electrode terminal(s) in the region between the distal tip of the electrode terminal(s) and the target tissue. The electrically conductive fluid may be a liquid, such as isotonic saline or blood, delivered to the target site, or a viscous fluid, such as a gel, applied to the target site. Since the vapor layer or vaporized region has a relatively high electrical impedance, it increases the voltage differential between the electrode terminal tip and the tissue and causes ionization within the vapor layer due to the presence of an ionizable species (e.g., sodium when isotonic saline is the electrically conducting fluid). This ionization, under optimal conditions, induces the discharge of energetic electrons and photons from the vapor layer and to the surface of the target tissue. This energy may be in the form of energetic photons (e.g., ultraviolet radiation), energetic particles (e.g., electrons) or a combination thereof. A more detailed description of this phenomena, termed Coblation™ can be found in commonly assigned U.S. Pat. No. 5,683,366 the complete disclosure of which is incorporated herein by reference.

The present invention applies high frequency (RF) electrical energy in an electrically conducting fluid environment to remove (i.e., resect, cut or ablate) a body structure, and to seal transected vessels within the region of the target tissue. The present invention is particularly useful for sealing larger arterial vessels, e.g., on the order of 1 mm or greater. In some embodiments, a high frequency power supply is provided having an ablation mode, wherein a first voltage is applied to an electrode terminal sufficient to effect molecular dissociation or disintegration of the tissue, and a coagulation mode, wherein a second, lower voltage is applied to an electrode terminal (either the same or a different electrode) sufficient to achieve hemostasis of severed vessels within the tissue. In other embodiments, an electrosurgical probe is provided having one or more coagulation electrode(s) configured for sealing a severed vessel, such as an arterial vessel, and one or more electrode terminals configured for either contracting the collagen fibers within the tissue or removing (ablating) the tissue, e.g., by applying sufficient energy to the tissue to effect molecular dissociation. In the latter embodiments, the coagulation electrode(s) may be configured such that a single voltage can be applied to coagulate with the coagulation electrode(s), and to ablate with the electrode terminal(s). In other embodiments, the power supply is combined with the coagulation probe such that the coagulation electrode is used when the power supply is in the coagulation mode (low voltage), and the electrode terminal(s) are used when the power supply is in the ablation mode (higher voltage).

The electrosurgical catheter will comprise a flexible body having a proximal end and a distal end which supports one or more electrode terminals. The catheter shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode or electrode array. The shaft will usually include a plurality of wires or other conductive elements running axially therethrough to permit connection of the electrode or electrode array and the return electrode to a connector at the proximal end of the shaft. The catheter may include a guide wire for guiding the catheter to the target site, or the catheter may comprise a steerable guide catheter. The catheter may also include a substantially rigid distal end portion to increase the torque control of the distal end portion as the catheter is advanced further into the patient's body. Specific shaft designs will be described in detail in connection with the figures hereinafter.

The electrode terminal(s) are preferably supported by an inorganic insulating support positioned near the distal end of the catheter body. The return electrode may be part of the catheter body, part of a separate movable guide wire or on another instrument. In the preferred embodiments, the return electrode comprises a separate movable guide wire positioned within an internal lumen of the catheter body. The proximal end of the catheter will include the appropriate electrical connections for coupling the return electrode and the electrode terminal(s) to a high frequency power supply, such as an electrosurgical generator.

The catheter will also include other internal lumens for providing separate functions, such as delivering fluid and aspirating products of ablation from the target site. Preferably, the catheter will have a fluid delivery lumen for delivering electrically conducting fluid to the target site, and an aspiration lumen coupled to a vacuum source for aspirating non-condensable gases and other products of ablation from the site.

The catheter will also preferably include an isolation system for fluidly isolating the region around the target site. In one embodiment, the isolation system includes proximal and distal balloons that are movable to portions of the body passage proximal and distal to the region of the target site. The distal balloon, by way of example, may be formed on a hollow guide wire that is fluidly coupled to an inflation source, such as a syringe. The proximal balloon, for example, may be coupled to the catheter body proximal to the active and return electrodes.

The invention typically includes guiding apparatus for guiding the catheter along a pathway approximating the central region of the occluded blood vessel. The guiding apparatus is usually an electrically conducting wire that may serve as the return electrode. The electrically conducting wire is extensible from the tip of the catheter and is located within and concentric to the catheter conveniently being in the form of a movable or fixed guidewire, usually being a movable guidewire.

The current flow path between the electrode terminal(s) and the return electrode(s) may be generated by submerging the tissue site in an electrical conducting fluid (e.g., within a viscous fluid, such as an electrically conductive gel) or by directing an electrically conducting fluid along a fluid path to the target site (i.e., a liquid, such as isotonic saline, or a gas, such as argon). The conductive gel may also be delivered to the target site to achieve a slower more controlled delivery rate of conductive fluid. In addition, the viscous nature of the gel may allow the surgeon to more easily contain the gel around the target site (e.g., rather than attempting to contain isotonic saline). A more complete description of an exemplary method of directing electrically conducting fluid between the active and return electrodes is described in U.S. Pat. No. 5,697,281, previously incorporated herein by reference. Alternatively, the body's natural conductive fluids, such as blood, may be sufficient to establish a conductive path between the return electrode(s) and the electrode terminal(s), and to provide the conditions for establishing a vapor layer, as described above.

In some procedures, it may also be necessary to retrieve or aspirate the electrically conductive fluid and/or the non-condensable gaseous products of ablation. In addition, it may be desirable to aspirate small pieces of tissue or occlusive media that are not completely disintegrated by the high frequency energy, or other fluids at the target site, such as blood, mucus, the gaseous products of ablation, etc. Accordingly, the system of the present invention will usually include one or more suction lumen(s) in the catheter, or on another instrument, coupled to a suitable vacuum source for aspirating fluids from the target site.

The present invention may use a single active electrode terminal or an array of electrode terminals spaced around the distal surface of the catheter. In the latter embodiment, the electrode array usually includes a plurality of independently current-limited and/or power-controlled electrode terminals to apply electrical energy selectively to the target tissue while limiting the unwanted application of electrical energy to the surrounding tissue and environment resulting from power dissipation into surrounding electrically conductive fluids, such as blood, normal saline, and the like. The electrode terminals may be independently current-limited by isolating the terminals from each other and connecting each terminal to a separate power source that is isolated from the other electrode terminals. Alternatively, the electrode terminals may be connected to each other at either the proximal or distal ends of the catheter to form a single wire that couples to a power source.

In one configuration, each individual electrode terminal in the electrode array is electrically insulated from all other electrode terminals in the array within said probe and is connected to a power source which is isolated from each of the other electrode terminals in the array or to circuitry which limits or interrupts current flow to the electrode terminal when low resistivity material (e.g., blood, electrically conductive saline irrigant or electrically conductive gel) causes a lower impedance path between the return electrode and the individual electrode terminal. The isolated power sources for each individual electrode terminal may be separate power supply circuits having internal impedance characteristics which limit power to the associated electrode terminal when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the electrode terminals through independently actuatable switches, or by independent current limiting elements, such as inductors, capacitors, resistors and/or combinations thereof. The current limiting elements may be provided in the probe, connectors, cable, controller or along the conductive path from the controller to the distal tip of the probe. Alternatively, the resistance and/or capacitance may occur on the surface of the active electrode terminal(s) due to oxide layers which form selected electrode terminals (e.g., titanium or a resistive coating on the surface of metal, such as platinum).

The tip region of the probe may comprise many independent electrode terminals designed to deliver electrical energy in the vicinity of the tip. The selective application of electrical energy to the conductive fluid is achieved by connecting each individual electrode terminal and the return electrode to a power source having independently controlled or current limited channels. The return electrode(s) may comprise a single tubular member of conductive material proximal to the electrode array at the tip which also serves as a conduit for the supply of the electrically conducting fluid between the active and return electrodes. Alternatively, the probe may comprise an array of return electrodes at the distal tip of the probe (together with the active electrodes) to maintain the electric current at the tip. The application of high frequency voltage between the return electrode(s) and the electrode array results in the generation of high electric field intensities at the distal tips of the electrode terminals with conduction of high frequency current from each individual electrode terminal to the return electrode. The current flow from each individual electrode terminal to the return electrode(s) is controlled by either active or passive means, or a combination thereof, to deliver electrical energy to the surrounding conductive fluid while minimizing energy delivery to surrounding (non-target) tissue.

The application of a high frequency voltage between the return electrode(s) and the electrode terminal(s) for appropriate time intervals effects cutting, removing, ablating, shaping, contracting or otherwise modifying the target tissue. The tissue volume over which energy is dissipated (i.e., a high current density exists) may be precisely controlled, for example, by the use of a multiplicity of small electrode terminals whose effective diameters or principal dimensions range from about 5 mm to 0.01 mm, preferably from about 2 mm to 0.05 mm, and more preferably from about 1 mm to 0.1 mm. Electrode areas for both circular and non-circular terminals will have a contact area (per electrode terminal) below 25 mm$^2$, preferably being in the range from 0.0001 mm$^2$ to 1 mm$^2$, and more preferably from 0.005 mm$^2$ to 0.5 mm$^2$. The circumscribed area of the electrode array is in the range from 0.25 mm$^2$ to 75 mm$^2$, preferably from 0.5 mm$^2$ to 40 mm$^2$, and will usually include at least two isolated electrode terminals, preferably at least five electrode terminals, often greater than 10 electrode terminals and even 50 or more electrode terminals, disposed over the distal contact surfaces on the shaft. The use of small diameter electrode terminals increases the electric field intensity and reduces the extent or depth of tissue heating as a consequence of the divergence of current flux lines which emanate from the exposed surface of each electrode terminal.

The area of the tissue treatment surface can vary widely, and the tissue treatment surface can assume a variety of geometries, with particular areas and geometries being selected for specific applications. Active electrode surfaces can have areas in the range from 0.25 mm$^2$ to 75 mm$^2$, usually being from about 0.5 mm$^2$ to 40 mm$^2$. The geometries can be planar, concave, convex, hemispherical, conical, linear "in-line" array or virtually any other regular or irregular shape. Most commonly, the active electrode(s) or electrode terminal(s) will be formed at the distal tip of the electrosurgical probe shaft, frequently being planar, disk-shaped, or hemispherical surfaces for use in reshaping procedures or being linear arrays for use in cutting. Alternatively or additionally, the active electrode(s) may be formed on lateral surfaces of the electrosurgical probe shaft (e.g., in the manner of a spatula), facilitating access to certain body structures in endoscopic procedures.

In some embodiments, the electrode support and the fluid outlet may be recessed from an outer surface of the catheter to confine the electrically conductive fluid to the region immediately surrounding the electrode support. In addition, the shaft may be shaped so as to form a cavity around the electrode support and the fluid outlet. This helps to assure that the electrically conductive fluid will remain in contact with the electrode terminal(s) and the return electrode(s) to maintain the conductive path therebetween. In addition, this will help to maintain a vapor or plasma layer between the electrode terminal(s) and the tissue at the treatment site throughout the procedure, which reduces the thermal damage that might otherwise occur if the vapor layer were extinguished due to a lack of conductive fluid. Provision of the electrically conductive fluid around the target site also helps to maintain the tissue temperature at desired levels.

The electrically conducting fluid should have a threshold conductivity to provide a suitable conductive path between the return electrode and the electrode terminal(s). The electrical conductivity of the fluid (in units of milliSiemans per centimeter or mS/cm) will usually be greater than 0.2 mS/cm, preferably will be greater than 2 mS/cm and more preferably greater than 10 mS/cm. In an exemplary embodiment, the electrically conductive fluid is isotonic saline, which has a conductivity of about 17 mS/cm.

The voltage difference applied between the return electrode(s) and the electrode terminal(s) will be at high or radio frequency, typically between about 5 kHz and 20 MHz, usually being between about 30 kHz and 2.5 MHz, preferably being between about 50 kHz and 500 kHz, more preferably less than 350 kHz, and most preferably between about 100 kHz and 200 kHz. The RMS (root mean square) voltage applied will usually be in the range from about 5 volts to 1000 volts, preferably being in the range from about 10 volts to 500 volts depending on the electrode terminal size, the operating frequency and the operation mode of the particular procedure or desired effect on the tissue (i.e., contraction, coagulation or ablation). For removal of occlusive media within body lumens, the voltage will usually be in the range of about 100 to 300 Vrms. Typically, the peak-to-peak voltage will be in the range of 10 to 2000 volts and preferably in the range of 20 to 500 volts and more preferably in the range of about 40 to 450 volts (again, depending on the electrode size, the operating frequency and the operation mode).

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with e.g., lasers claiming small depths of necrosis, which are generally pulsed about 10 to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of target tissue being heated, and/or the maximum allowed temperature selected for the probe tip. The power source allows the user to select the voltage level according to the specific requirements of a particular cardiac surgery, arthroscopic surgery, dermatological procedure, ophthalmic procedures, open surgery or other endoscopic surgery procedure. For cardiac procedures, the power source may have an additional filter, for filtering leakage voltages at frequencies below 100 kHz, particularly voltages around 60 kHz. A description of a suitable power source can be found in U.S. Provisional Application No. 60/062,996, filed on Oct. 23, 1997.

The power source may be current limited or otherwise controlled so that undesired heating of the target tissue or surrounding (non-target) tissue does not occur. In a presently preferred embodiment of the present invention, current limiting inductors are placed in series with each independent electrode terminal, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in U.S. Pat. No. 5,697,909, the complete disclosure of which is incorporated herein by reference. Additionally, current limiting resistors may be selected. Preferably, these resistors will have a large positive temperature coefficient of resistance so that, as the current level begins to rise for any individual electrode terminal in contact with a low resistance medium (e.g., saline irrigant or blood), the resistance of the current limiting resistor increases significantly, thereby minimizing the power delivery from said electrode terminal into the low resistance medium (e.g., saline irrigant or blood).

In yet another aspect of the invention, the control system is "tuned" so that it will not apply excessive power to the blood (e.g., in the ventricle), once it crosses the wall of the heart and enters the chamber of the left ventricle. This minimizes the formation of a thrombus in the heart (i.e., will not induce thermal coagulation of the blood). The control system may include an active or passive architecture, and will typically include a mechanism for sensing resistance between a pair(s) of active electrodes at the distal tip, or between one or more active electrodes and a return electrode, to sense when the electrode array has entered into the blood-filled chamber of the left ventricle. Alternatively, current limiting means may be provided to prevent sufficient joulean heating in the lower resistivity blood to cause thermal coagulation of the blood. In another alternative embodiment, an ultrasound transducer at the tip of the probe can be used to detect the boundary between the wall of the heart and the blood filled left ventricle chamber, turning off the electrode array just as the probe crosses the boundary.

It should be clearly understood that the invention is not limited to electrically isolated electrode terminals, or even to a plurality of electrode terminals. For example, the array of active electrode terminals may be connected to a single lead that extends through the catheter shaft to a power source of high frequency current. Alternatively, the catheter may incorporate a single electrode that extends directly through the catheter shaft or is connected to a single lead that extends to the power source. The active electrode(s) may have ball shapes (e.g., for tissue vaporization and desiccation), twizzle shapes (for vaporization and needle-like cutting), spring shapes (for rapid tissue debulking and desiccation), twisted metal shapes, annular or solid tube shapes or the like. Alternatively, the electrode(s) may comprise a plurality of filaments, rigid or flexible brush electrode(s) (for debulking a tumor, such as a fibroid, bladder tumor or a prostate adenoma), side-effect brush electrode(s) on a lateral surface of the shaft, coiled electrode(s) or the like.

In one embodiment, an electrosurgical catheter comprises a single active electrode terminal that extends from an insulating member, e.g., ceramic, at the distal end of the shaft. The insulating member is preferably a tubular structure that separates the active electrode terminal from a tubular or annular return electrode positioned proximal to the insulating member and the active electrode. In another embodiment, the catheter includes a single active electrode that can be rotated relative to the rest of the catheter body, or the entire catheter may be rotated relative to the body lumen.

Referring to the drawings in detail, wherein like numerals indicate like elements, a lumen recanalization catheter system 2 is shown constructed according to the principles of the present invention. Catheter system 2 generally comprises an electrosurgical catheter 6 connected to a power supply 80 by an interconnecting cable 86 for providing high frequency voltage to a target tissue and an irrigant reservoir or source 100 for providing electrically conducting fluid to the target site. Catheter 6 generally comprises an elongate, flexible shaft body 12 including a tissue ablating region 8 at the distal end of body 12, and a proximal balloon 40 positioned on body 12 proximal to region 8. In a specific embodiment, a guide wire 28 (which may also serve as a return electrode) includes a distal balloon 18 which may be axially translated relative to region 8 and proximal balloon 40, as discussed in further detail below.

The proximal portion of catheter 6 includes a multi-lumen fitment 114 which provides for interconnections between lumens and electrical leads within catheter 6 and conduits and cables proximal to fitment 114. By way of example, a catheter electrical connector 96 is removably connected to a distal cable connector 94 which, in turn, is removably connectable to generator 80 through connector 92. One or more electrically conducting lead wires (not shown) within catheter 6 extend between one or more active electrodes at tissue ablating region 8 and one or more corresponding electrical terminals (also not shown) in catheter connector 96 via active electrode cable branch 87. In the illustrative embodiment, hollow guide wire 28 functions as the return electrode, and is electrically attached within a contact housing 111 by a sliding electrical contact (not shown). A return electrode cable branch 89 couples the sliding electrical contact to catheter connector 96. Electrical leads within cable 86 allow connection between terminals corresponding to return electrode 28 and one or more active electrodes 32 in distal cable connector 94 and generator 80.

Power supply 80 has an operator controllable voltage level adjustment 82 to change the applied voltage level, which is observable at a voltage level display 84. Power supply 80 also includes a foot pedal 88 and a cable 90 which is removably coupled to power supply 80 for remotely adjusting the energy level applied to electrode terminals. In an exemplary embodiment, power supply 80 includes three such foot pedals (not shown), wherein the first foot pedal is used to place the power supply into the "ablation" mode and the second foot pedal places power supply 80 into the "subablation" mode. The third foot pedal allows the user to adjust the voltage level within the "ablation" mode. In the ablation mode, a sufficient voltage is applied to the electrode terminals to establish the requisite conditions for molecular dissociation of the tissue (i.e., vaporizing a portion of the electrically conductive fluid, ionizing charged particles within the vapor layer and accelerating these charged particles against the tissue). As discussed above, the requisite voltage level for ablation will vary depending on the number, size, shape and spacing of the electrodes, the distance in which the electrodes extend from the support member, etc. Once the surgeon places the power supply in the "ablation" mode, voltage level adjustment 82 or the third foot pedal may be used to adjust the voltage level to adjust the degree or aggressiveness of the ablation.

Of course, it will be recognized that the voltage and modality of the power supply may be controlled by other input devices. However, applicant has found that foot pedals are convenient methods of controlling the power supply while manipulating the probe during a surgical procedure.

In the subablation mode, the power supply 80 applies a low enough voltage to the electrode terminals to avoid vaporization of the electrically conductive fluid and subsequent molecular dissociation of the tissue. The surgeon may automatically toggle the power supply between these modes by alternatively stepping on the foot pedals. This allows the surgeon to quickly move between subablation (e.g., coagulation) and ablation in situ, without having to remove his/her concentration from the surgical field or without having to request an assistant to switch the power supply. By way of example, as the surgeon is sculpting soft tissue in the ablation mode, the probe typically will simultaneously seal and/or coagulation small severed vessels within the tissue. However, larger vessels, or vessels with high fluid pressures (e.g., arterial vessels) may not be sealed in the ablation mode. Accordingly, the surgeon can simply step on the appropriate foot pedal, automatically lowering the voltage level below the threshold level for ablation, and apply sufficient pressure onto the severed vessel for a sufficient period of time to seal and/or coagulate the vessel. After this is completed, the surgeon may quickly move back into the ablation mode by stepping on a foot pedal.

Figure 13:
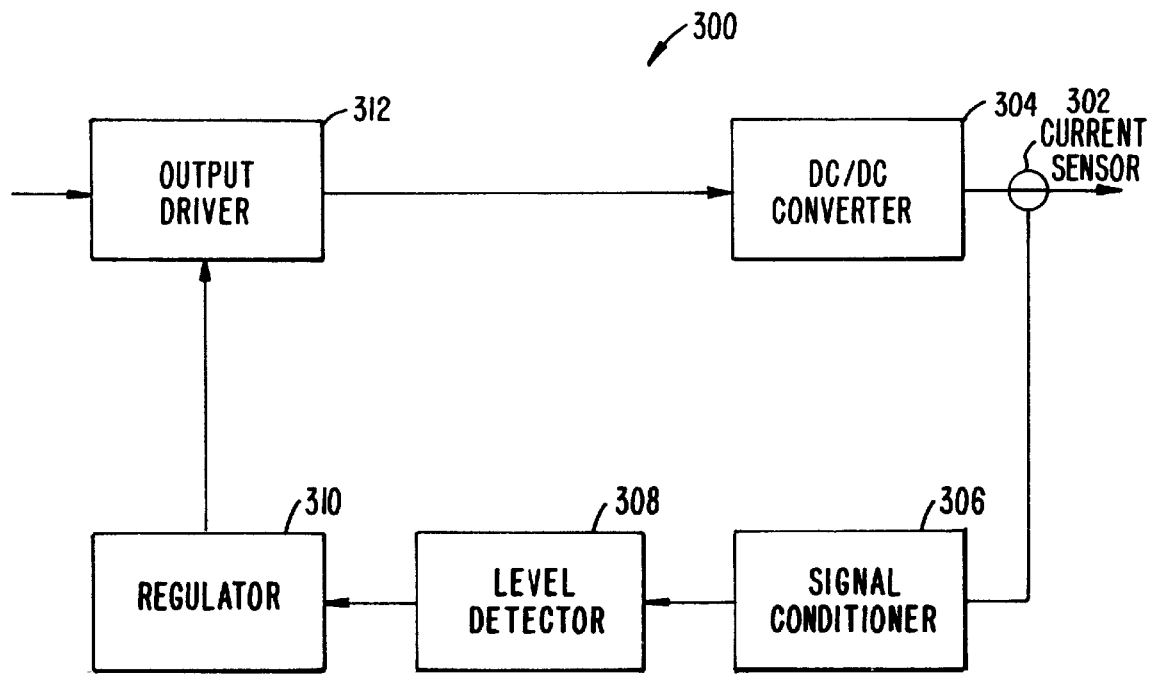
FIG. 13 is a block diagram of a power limiting device according to the present invention.

Referring now to FIGS. 13–22, an exemplary power supply will be described. The power supply 28 of the present invention may include power limiting devices to protect attached electrosurgical catheters from excessive power delivery and to sustain controlled probe operation. Power is the time rate of transferring or transforming energy, and for electricity, power is measured in watts, where one watt is the power to create energy at the rate of one joule per second. Referring to FIG. 13, the power limiting device 300 is designed to reduce the power drawdown from the power supply 28 when an attached device such as a monopolar or bipolar surgical instrument is not engaging body tissue or draws excessive power. For example, excessive power is delivered from the power supply 28 if the RF catheter is in saline or blood and is not engaging target media. Device 300 conveniently conserves power used in the probe without completely deactivating the power supply 28 or requiring the user to manually reduce power. Excessive power draw will overheat the power supply and corrupt power supply performance. Device 300 also acts as a safety feature by reducing the stray emission of energy when the probe is in transit through the body to a target site.

Figure 14:
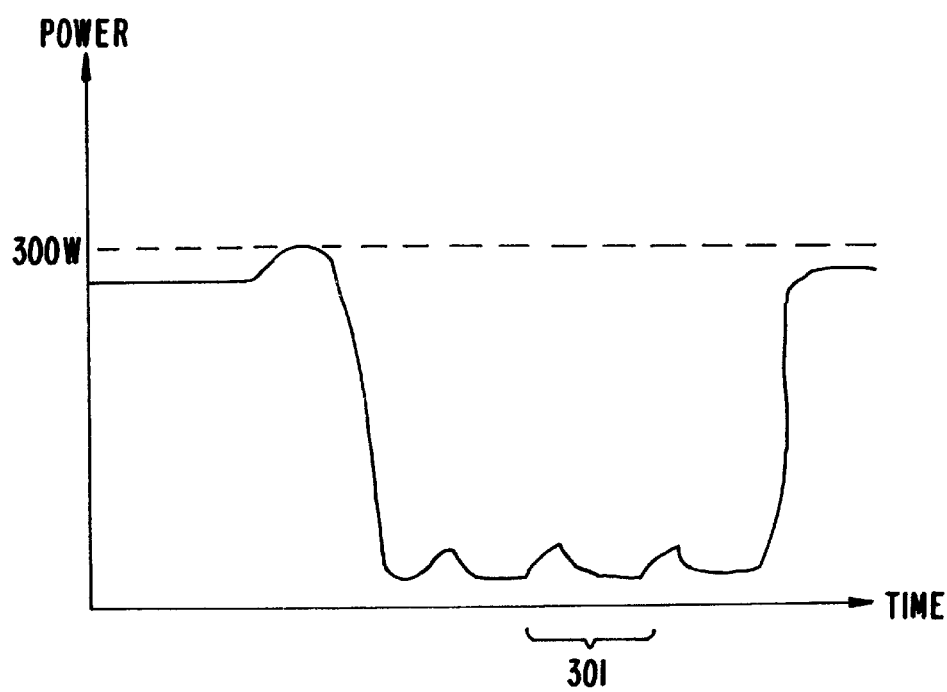
FIG. 14 is a graph of the power output of the power supply during normal operations and standby mode.

In general terms, the power limiting device 300 operates on a continuous basis to detect excessive power output. The device 300 is responsive to the "total power" delivered by the device. FIG. 14 illustrates the power output of the power supply 28 when an excessive power is detected. Device 300 limits the overall output power from the controller to be lower than about 240–360 watts, preferably about 300 watts. Once power output exceeds a predetermined threshold level, the device 300 then operates on a duty cycle or periodic detection cycle 301 between about 50 and 300 ms, where the device 300 checks every cycle to determine if it is safe to resume power output. Preferably, the device 300 has a fixed duty cycle wave form and includes a fixed periodical pulsing circuit which is about 10 ms on and 90 ms off. Once the fault condition is gone, power output returns to operating levels.

In one embodiment (FIG. 13), the device 300 uses a current sensor 302 attached to the output electrodes to derive the power output of the power supply 28. The current limit, which may be set at any desire level, is about 5 amps for a 300 watt power limit when voltage is set at about 60V. When current output reaches 5 amps, the device 300 reduces the output of the power supply to a standby mode. Once in standby mode, the power supply preferably has a pulsatile power output. As shown in FIG. 16, the device 300 allows the current output to be activated during each duty cycle to determine if the power supply may return to normal operation.

Figure 15:
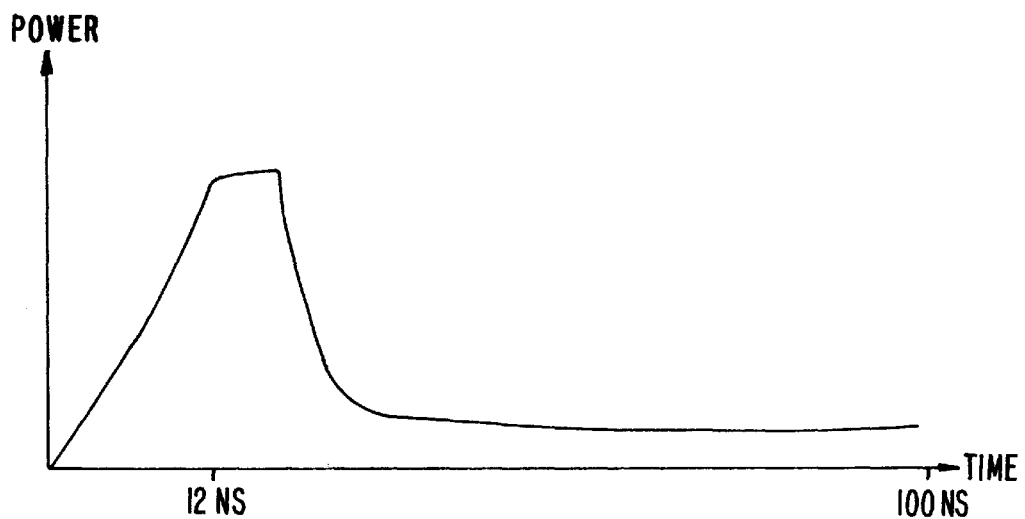
FIG. 15 is a graph of the power output of the power supply in a low power, pulsatile mode.

When in the standby mode, the pulsatile power output may be described as shown in FIG. 15. In the pulsatile mode, the duty cycle is about 10–15 ms on, preferably about 12 ms on, and about 85–90 ms off, preferably about 88 ms off. This creates a cycle of about 100 ms, during which time, power is increased and then reduced if the probe senses that it is not in the vicinity of body tissue or other higher impedance material. This sensing step is the initial portion of the duty cycle where current is activated for a period of time, described as being between 10–15 ms. If current again reaches the 5 amp level or some other predetermined level, the output is reduced and the device 300 waits for the next duty cycle. The total power output during this short period is only about 10 watts. However, the current output is sufficient to show that the fault condition still exists. Thus, when in the standby mode, the device 300 tests for potentially excessive power output with a fault condition that occurs without actually reaching the power level against which the device is protecting. This pulsatile power output continues until power drawdown returns to within acceptable ranges (FIG. 14). The power limiting reduces power output on a fault condition that is current based (so long as there is constant voltage).

Alternatively, the power limiting device 300 in the standby mode checks the impedance (instead of current) encountered by the probe every 100 ms or over some other interval selected by the user. As long as the probe is in a low impedance environment and impedance is below a predetermined level, the power supply will operate in the pulsatile mode, never fully activating to therapeutic power levels such as for ablation or coagulation. The low impedance is indicative of a potential over power scenario. In alternative embodiments, the device 300 may check the impedance over variable time intervals that change as desired. When the probe reaches a target site or comes in the vicinity of higher impedance tissue, in one embodiment, a higher impedance is noted by a drop in current draw (i.e. power draw) from the probe, signaling the regulator or logic unit 310 to increase power on the current or the next duty cycle. This brings the power supply out of the pulsatile mode. The power limiting device 300, however, will continue to check the impedance encountered every duty cycle.

Figure 16A:
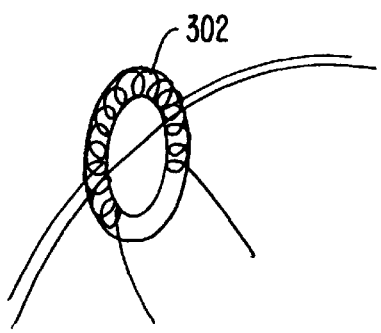
FIGS. 16A–16C show various embodiments of a current sensor.
Figure 16C:
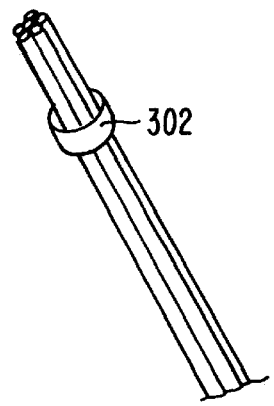
Figure 16B:
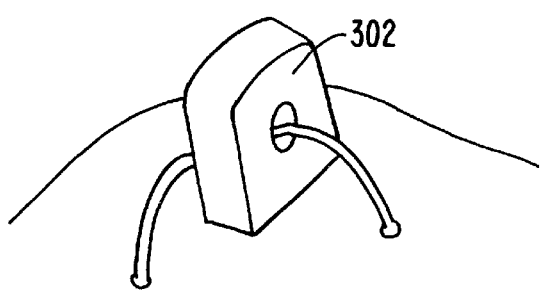

Referring to FIGS. 16A–16C, a preferred embodiment of the device 300 comprises of at least one current sensor 302 detecting the current output from DC/DC converter 304. The current sensor 302 may be configured as one sensor for one electrode or one sensor for a plurality of electrodes. In the present embodiment, one sensor 302 is used for six electrodes on the probe, although more preferably one sensor is used for three electrodes. Typically, the sensors 302 (noted as T1, T4, T5, etc.) are configured to wrap around the electrodes as shown in FIG. 16. Signals from sensors 302 are passed through a plurality of rectifying diodes and capacitors which filter and condition the ,typically analog signal from the current sensor. In the block diagram of FIG. 13, these diodes and components are represented by signal conditioner 306. The conditioned signal from the sensor 302 is then passed to a voltage comparator 308. The comparator 308 determines if the current output has exceed the predetermined threshold level. A logic unit 310 then determines power of output drive 312 based on the value of the output current compared to a predetermined current value. In the standby or power limited mode, the logic unit 310 of the device 300 will preferably duty cycle the output from output drive 312. Although the logic unit 310 is preferably an integrated circuit such as a Field Programmable Gate Array (FPGA) to maximize cost efficiency, it should be understood that other devices such as computers or microprocessors may also be used to perform the required logic functions.

Figure 17A:
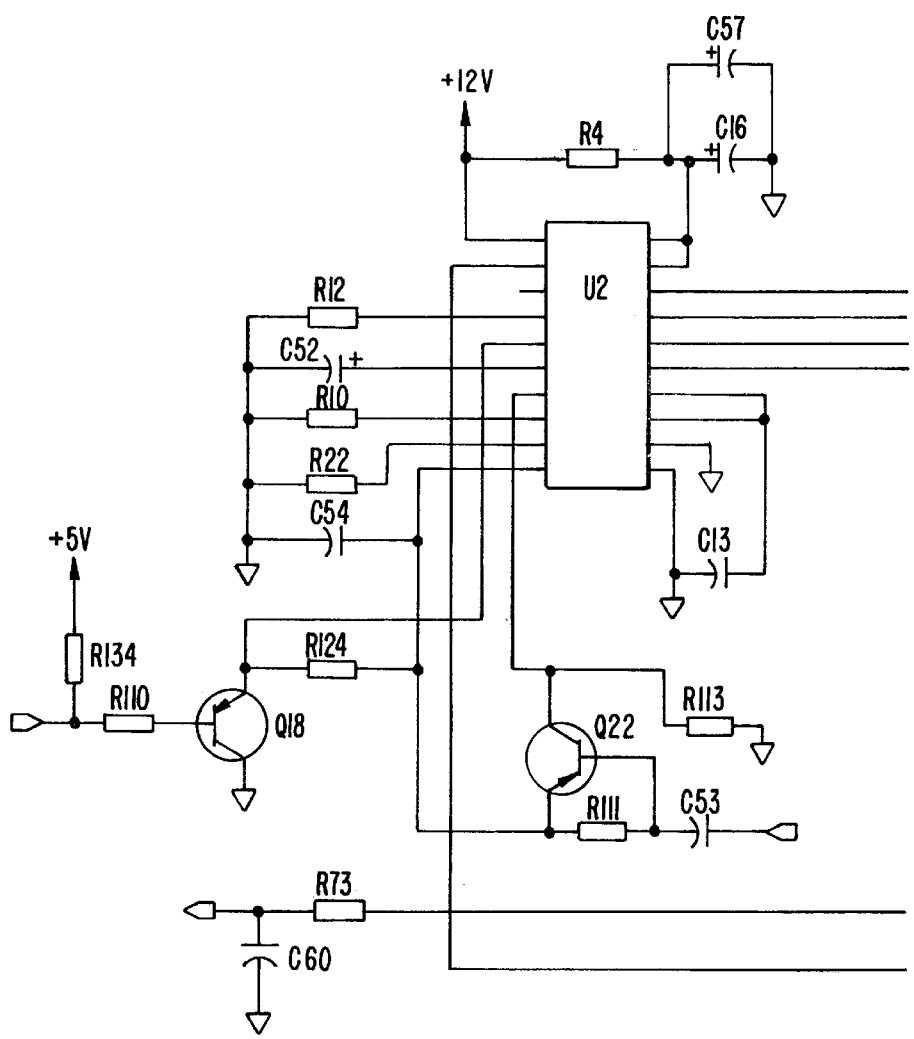
FIG. 17 is a circuit schematic of an exemplary embodiment of a power limiting device.
Figure 17:
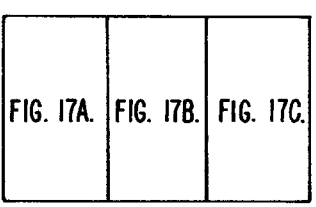
Figure 17B:
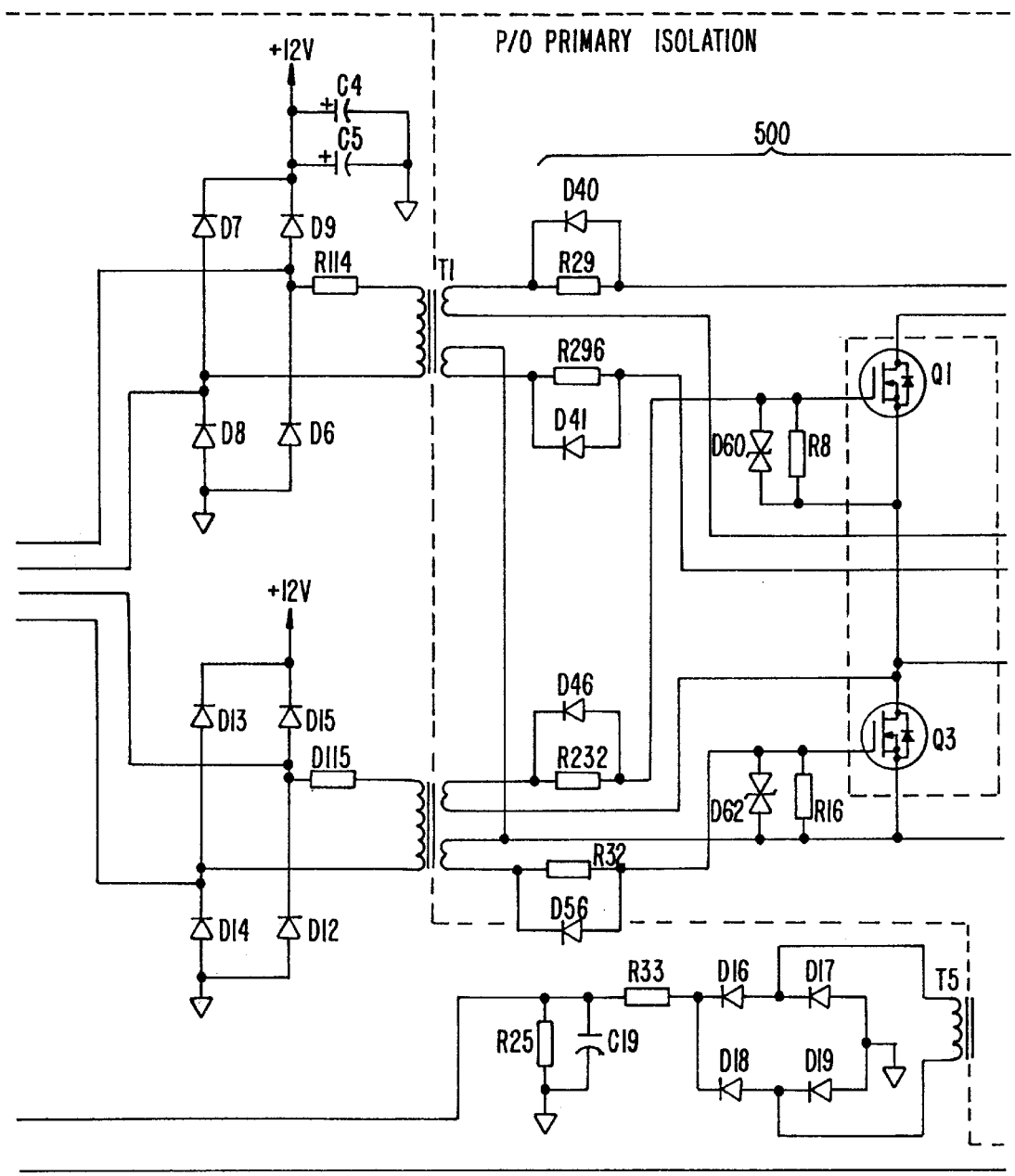
Figure 17C:
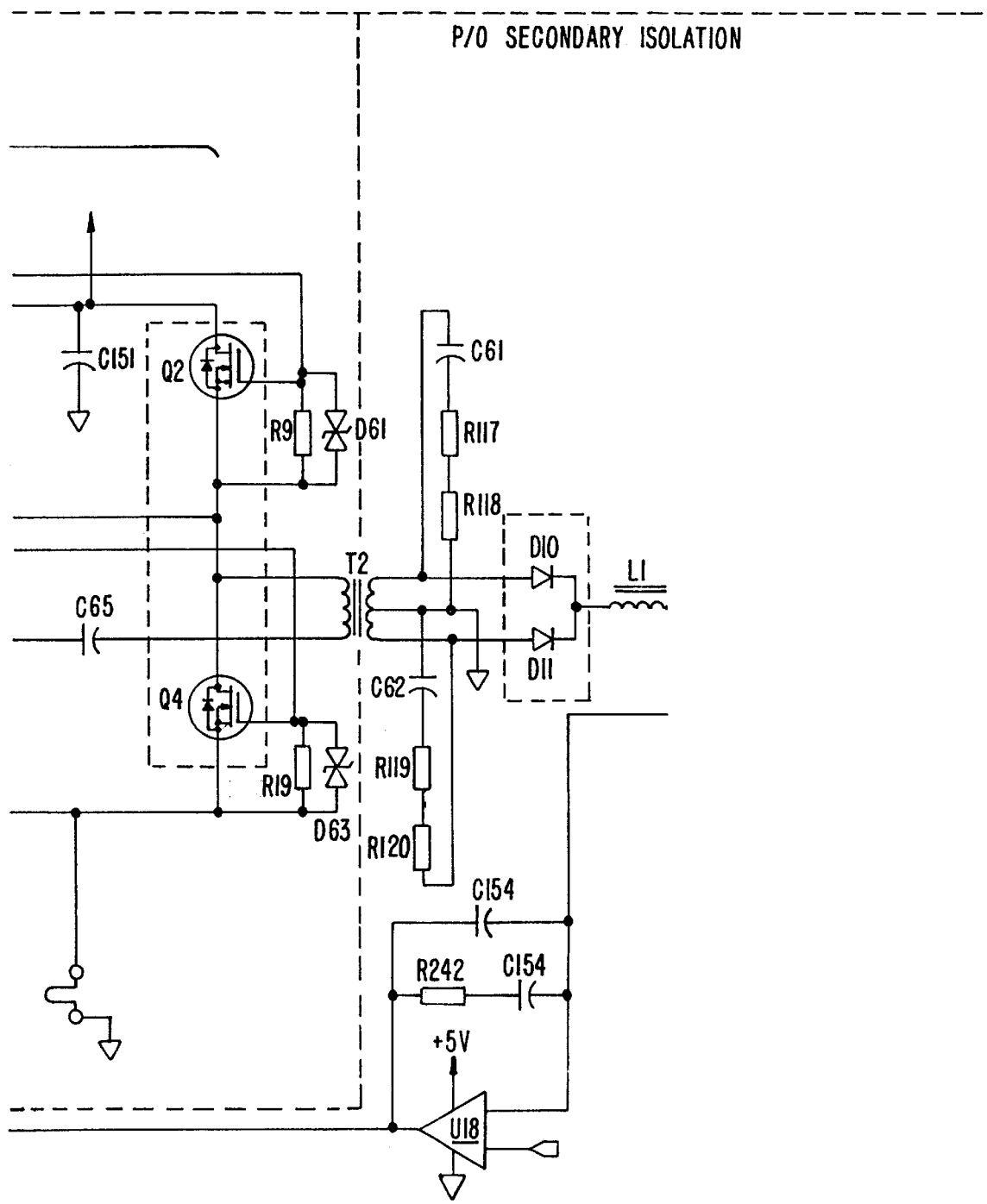

FIG. 17 shows an exemplary embodiment of power limiting device 300. The circuit diagram shows that overcurrent is sensed by T5. It is rectified and filtered by D16, D17, D18, D19, R33, and C19 etc. The rectified and filtered signals are fed into voltage comparator which determines if power threshold has been reached. The output of the comparator is fed into the FPGA which controls the power supply 28 to the power limiting mode (e.g. it turns of DC/DC converter 10 ms on and 90 ms off). Device 300 includes an converter of a full-wave bridge arrangement with all four switching element driven by a single transformer. It is capable, through the antiparallel diodes within the MOSFETs, of four-quadrant operation, returning reactive load energy to the power supply for self-protection. 100 kHz sync arrives as 500 nanosecond pull-up pulses from a differentiation network connected to the FPGA. The FPGA also exerts direct on/off control via DC_EN. The output smoothly ramps to regulation when allowed by the FPGA. Options for current limiting are provided. Both linear and digital (pulsatile) limiting are possible. Current limits may also respond to FPGA commands and change under logic control. The inverter is running at zero voltage switching mode to reduce EMI and indirectly reduces leakage current. A cycle-by-cycle current limit circuit serves to protect the switching elements from energy stored in filter and bypass capacitors. Cycle-by-cycle current limit control is applied by the FPGA removing the gate drive. The inverter runs at a fixed 50% duty cycle whenever drive (of about 100 kHz or other) from the FPGA is available. The inverter is running at zero voltage switching mode to reduce EMI and indirectly reduces leakage current.

The power supply 28 of the present invention may also include a spark limiting device 330 to prevent sudden current spikes which may char or otherwise damage the RF probe and surgical target site. For example, when an RF probe attached to the power supply touches a metallic object, the impedance encountered by the probe (relative to human tissue) decreases suddenly and this undesirably draws a large amount of current from the power supply. This sudden current increase may create sparks between the probe and the metal object. The large amount of current passing through the probe will likely char items along the electrical pathway and may melt electrodes on the electrosurgical probe.

Figure 18:
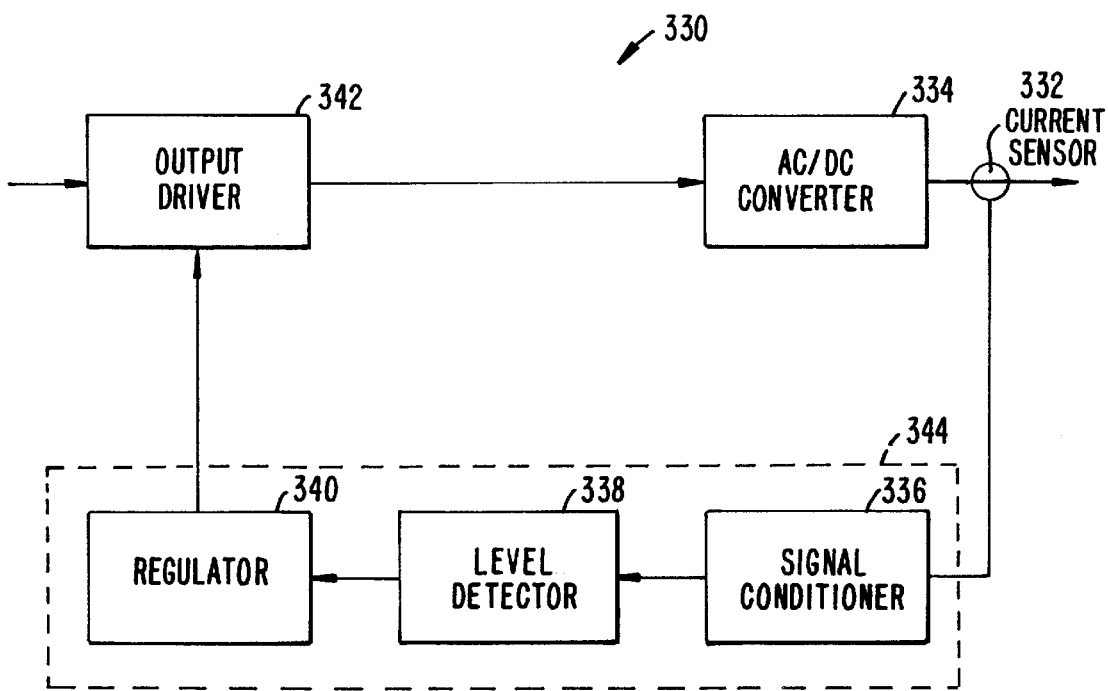
FIG. 18 is a block diagram of a spark limiting device according to the present invention.
Figure 19:
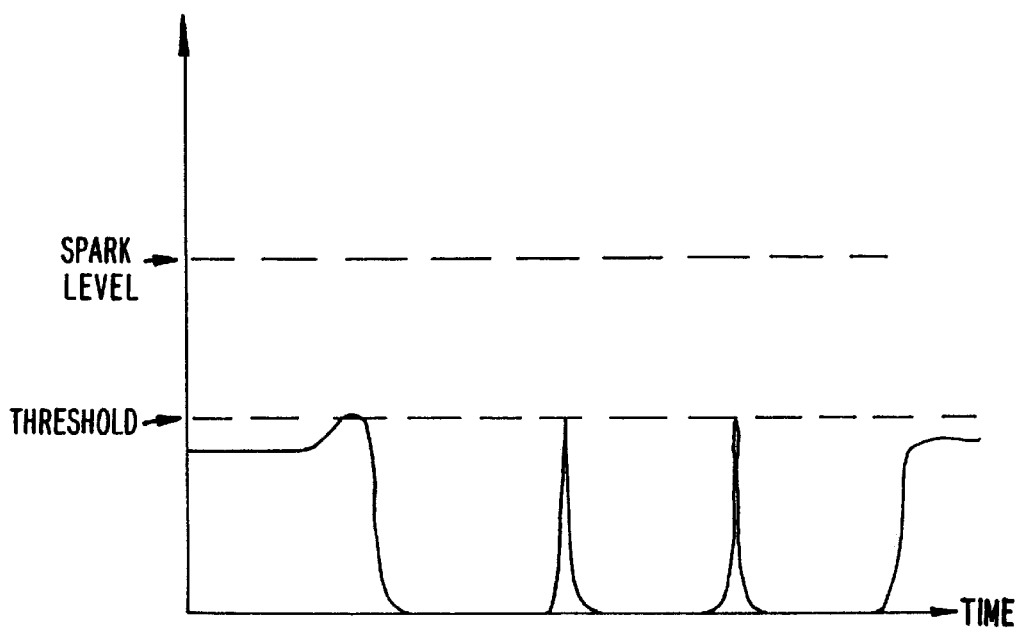
FIG. 19 is a chart of the current output of a spark limiting device according to the present invention.

Referring now to FIG. 18, the spark limiting device 330 will be described in detail. In general terms, the spark limiting device 330 will reduce current output to zero when an extremely low impedance source such as a metal screw or a metal cannula creates a high current drawdown. The spark limiting device 330 is located much closer to the output electrode. This reduces the delay of the device 330 and allows the device to respond more quickly. The spark limiting device 330 is directed to reduce current output to prevent sparking, not total power output. Although the block diagram of FIG. 10 appears similar to that of the power limiting device 300, the spark limiting device 330 is not a fixed periodical pulsing circuit of the type described in FIG. 17. The spark limiting device 330 preferably processes continuous signals, such as analog signals, from the current sensor 332. The spark limiting device 330 continuously monitors current fluctuations of the power output of converter 334 (typically an AC/DC converter). The continuous flow of signal in the spark limiting device 330 allows it to detect the sudden increase in current almost instantaneously and almost certainly before the isolated, power limiting device 300. Current output is preferably turned off after an overcurrent is detected.

The current output during normal therapeutic operation may be in the range of 0.2 amperes or less. The spark limiting device 330 preferably interrupts output when current exceeds about 1.0 to 3.0 amperes. These current levels are insufficient to cause sparking, but enough to warrant concern over potential sparking. When current exceeds levels higher than those stated, the device 330 will preferably prevent any current output from the probe. The output of the power supply 28 is similar to that of FIG. 19. In one embodiment, the spark limiting device 330 has a built-in delay device that turns off current output for a duration of 2–90 ms. Preferably, the delay is programmed into the FPGA. At the end of the delay period, the device 330 will allow current to flow through the probe, albeit at extremely low power, to detect if the extremely low impedance state still exists. If current again exceeds the threshold level of about 1.0 to 3.0 amperes (FIG. 19), the device 330 will zero the output of the power supply and pause for the built-in delay. This delay acts in some ways to give the spark limiting device a duty cycle-like operation.

It should be understood that although no current, preferably, is being emitted from the probe during the delay period, the power supply does not shutoff. This is particularly useful as this eliminates down time associated with restarting the power supply from poweroff. As soon as the probe is removed from the area of extremely low impedance, the spark limiting device 330 will allow power to flow from the RF probe as usual. Preferably, as long as the probe is exposed to the low impedance source, the device 330 will not allow power to be transmitted. Of course, it may be possible to configure the spark limiting device 330 to allow a low level of current to be emitted, versus shutting off the power output completely.

Figure 20:
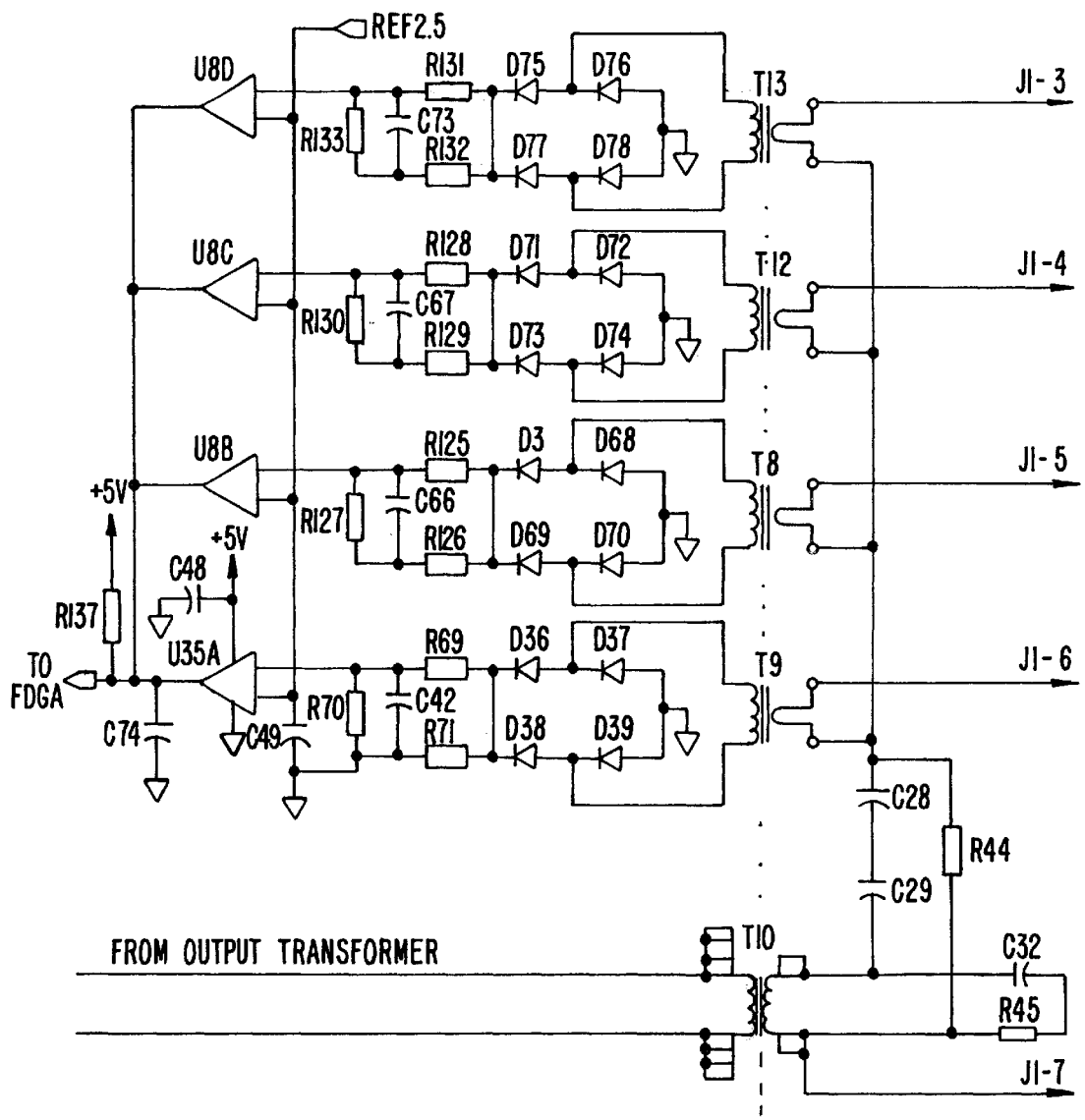
FIG. 20 is a circuit schematic of an exemplary embodiment of a spark limiting device.

The block diagram of FIG. 18 shows that the spark limiting device 330 includes a signal conditioner 336, a level detector 338, a regulator or logic unit 340, and an output driver 342 (such as an RF source known in the art). Although the preferred embodiment of the spark limiting device 330 is based on analog signals, it should be understood that the device 330 may be adapted to used analog signals or digital signals with extremely short duty cycles to approximate a continuous system. The logic device 340, level detector 338, and signal conditioner 336 may all be combined into a single device or processor as indicated by the dotted line 344. The same may also apply to the power limiting device 300 which has components that may be integrated together. Referring to FIG. 20, a circuit diagram of the spark limiting device 330 is shown. The current sensors 332 are denoted by elements T8, T9, T12, and T13. The diodes D36–D76 and resistors/capacitors R131–R133/C73 etc. are used to condition the analog signal to remove noise and other undesirable qualities. A voltage comparator U8D and the FPGA, corresponding to level detector 338 and logic device 340, are used to determine if the output current detected by sensor 332 is above a predetermined level.

Figure 21:
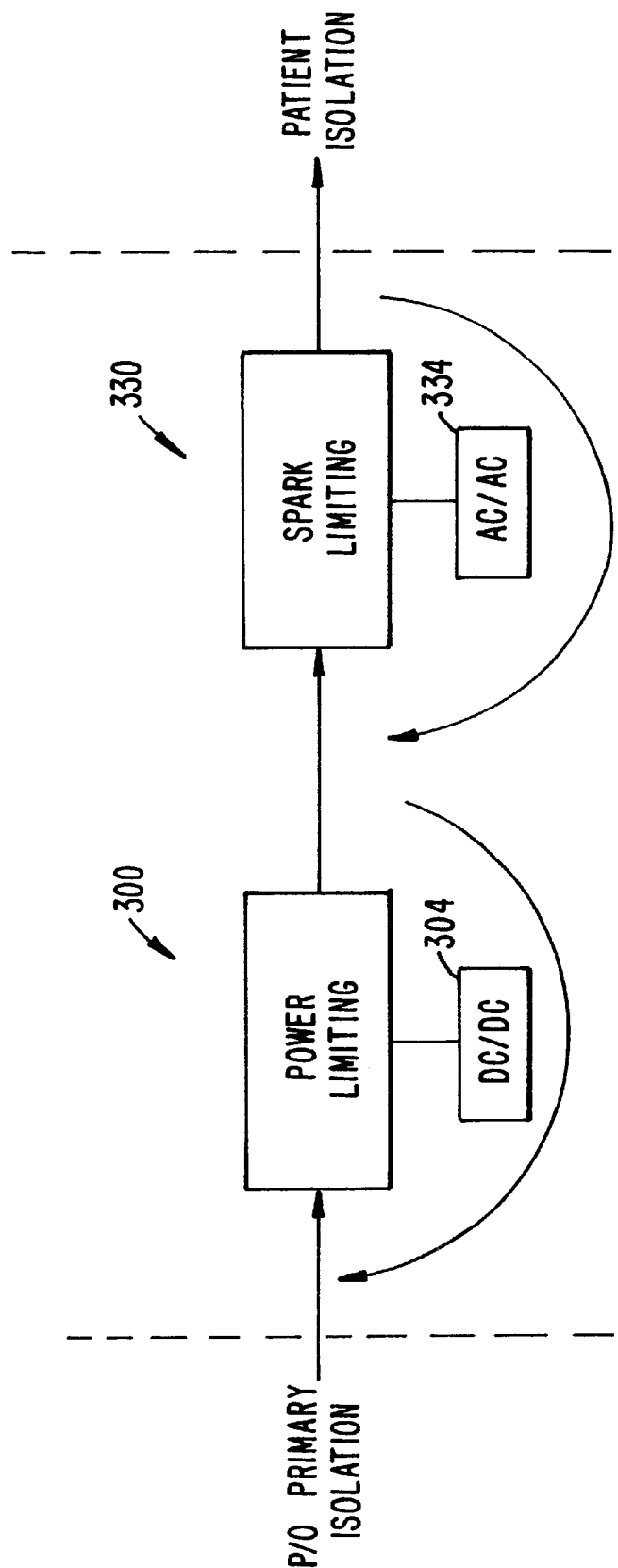
FIG. 21 is a block diagram of the relationship between power limiting and spark limiting devices.
Figure 22A:
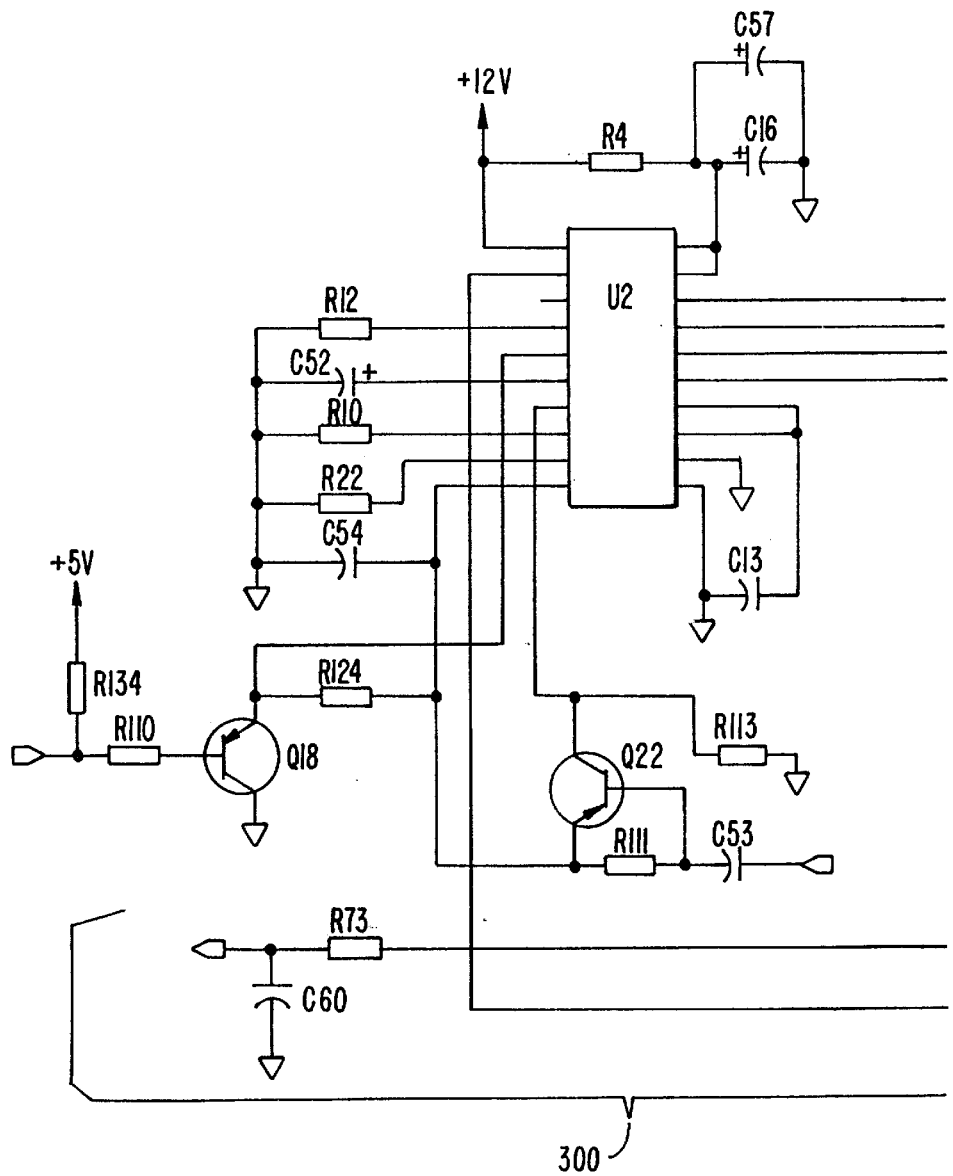
FIG. 22 is a circuit schematic showing both the power limiting and spark limiting devices.
Figure 22B:
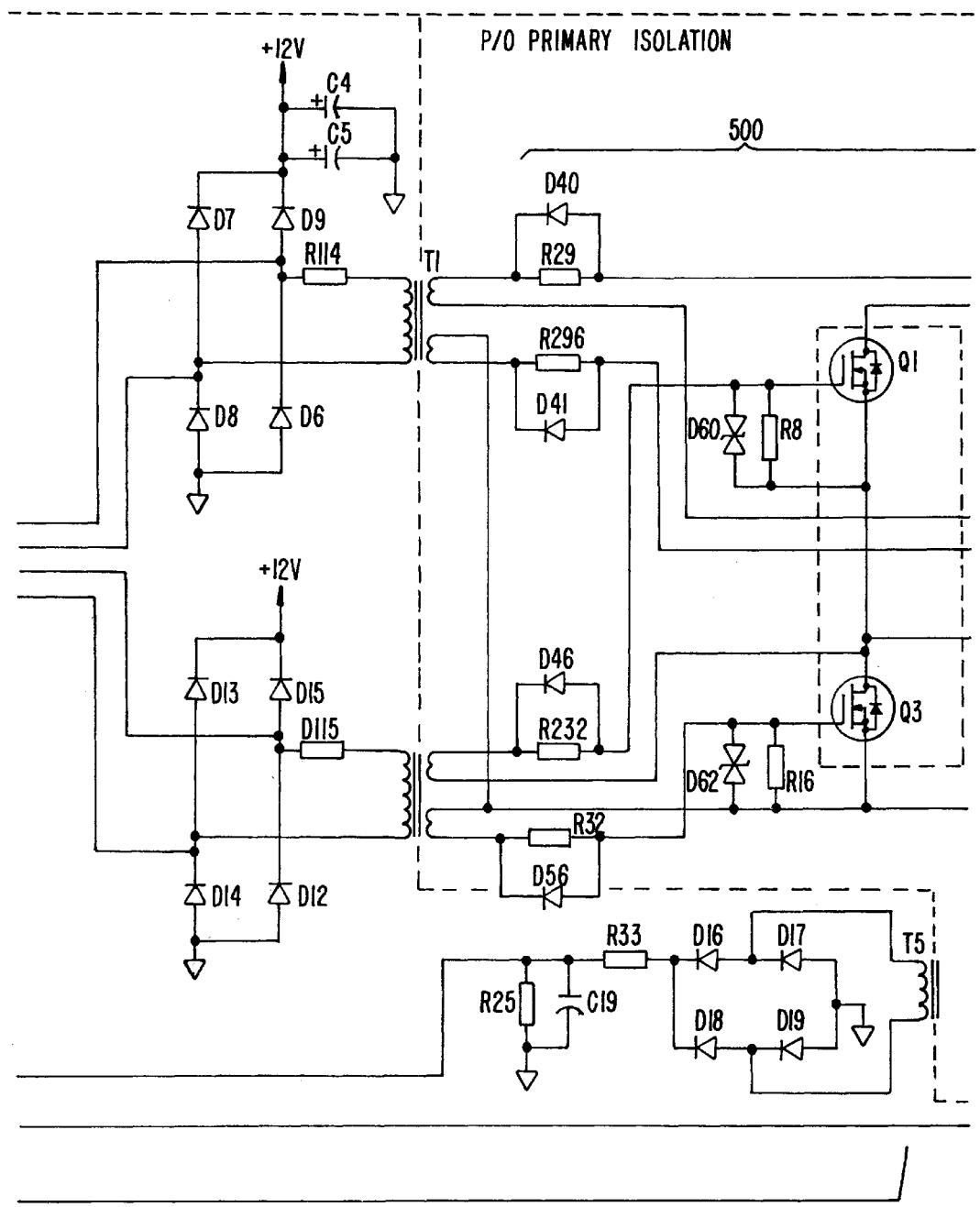
Figure 22C:
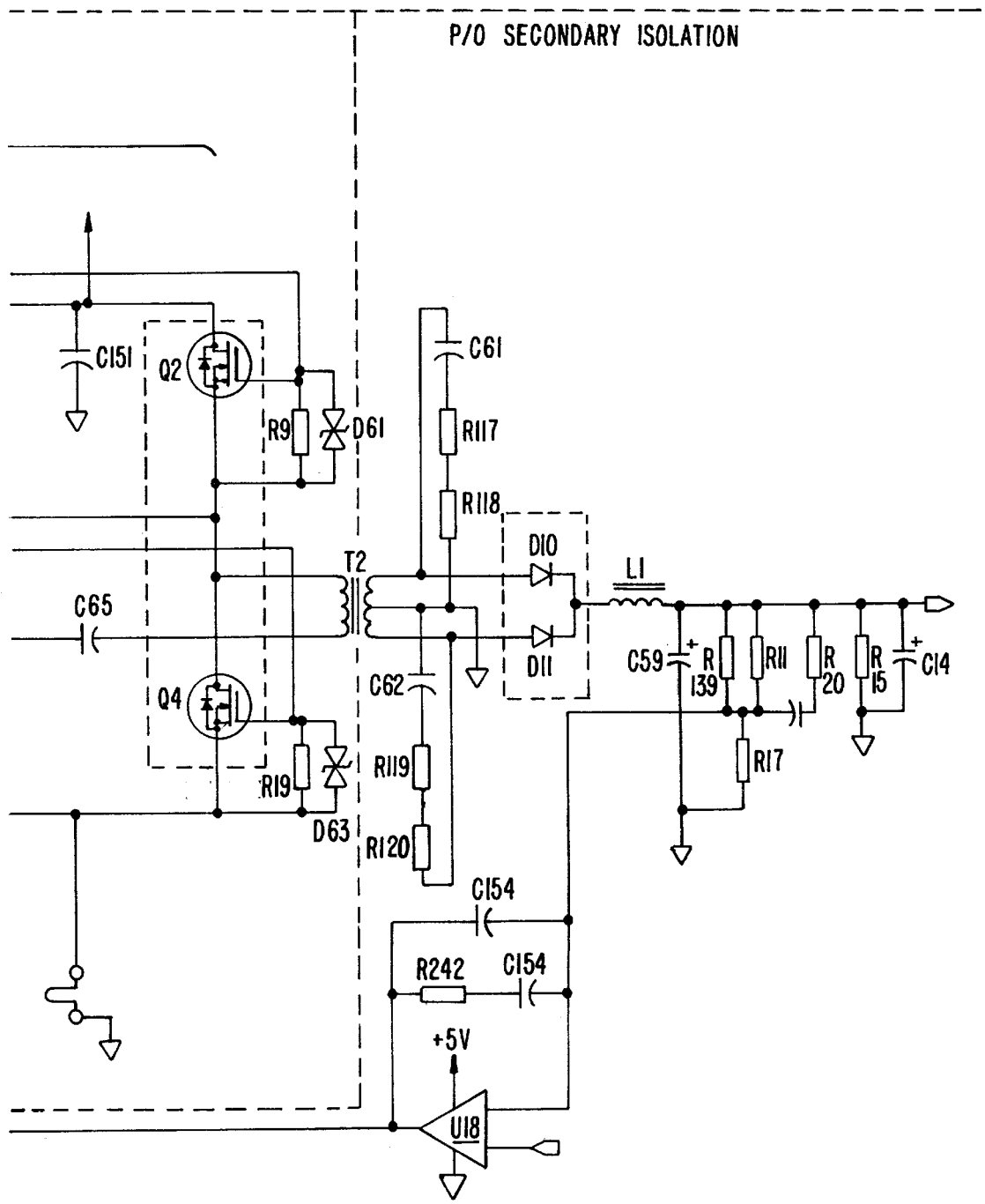
Figure 22D:
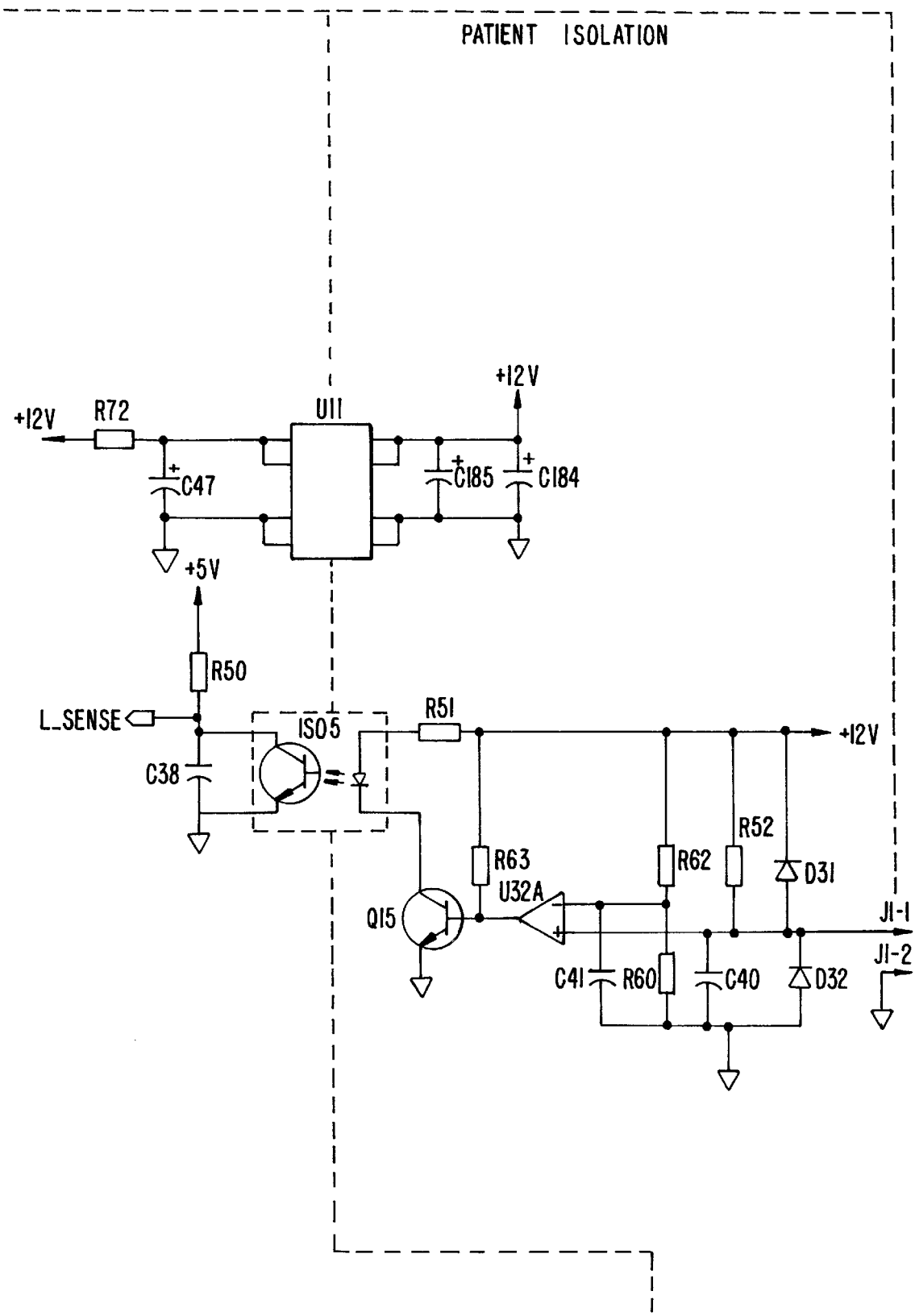

Although the power limiting device 300 and the spark limiting device 330 may be used individually, it is understood that the two devices may also be used concurrently in the power supply. In a preferred embodiment, the power supply of the present invention has the power limiting device 300 and the spark limiting device 330 arranged in a serial configuration as shown in FIG. 21–22. This configuration provides for the circuit isolation mandated by safety regulations for medical device power supplies. As shown in FIG. 14, the power supply 28 has P/O primary isolation, P/O secondary isolation, and patient isolation. Using devices 300 and 330 also provides protection for both converters (DC/DC and DC/AC) used to provide stability of the power output. Due to the various isolation barriers required to meet safety and regulatory standards for medical device power supplies, the spark limiting device 330 is typically located closer to the electrode output while the power limiting device 300 is more isolated from the electrode output. The additional amount of isolation circuitry to introduces a lag time into the responsiveness of the power limiting device. Thus, one device reacts slower and while the device closer to the electrode reacts faster. In one embodiment, there is about a 200 ms delay in order for the current to reach the power limiting device 300.

As an example of how the devices would function together, when an attached RF catheter touches a metallic object, such as a stent within a body passage, the spark limiting device 330 activates to reduce the current output from the power supply to zero. The current output may be reduced to some nonzero value so long as sparks are not generated. The spark limiting device 330 introduces a delay and then checks to see if it can power up. During this time, the power limiting device 300 also continues to check about every duty cycle to see if power should be increased. In one embodiment, the power limiting device 300 introduces more delay into the system since its duty cycle is longer than the 2–90 ms delay of the spark limiting device. As soon as the probe is removed from the extremely low impedance site and current drawdown stays within acceptable ranges, the probe resumes normal operations. If the catheter is no longer in contact with target tissue, then the generator will most likely be in pulsatile mode while awaiting to be repositioned.

Referring again to FIG. 1, conductive fluid 30 is provided to tissue ablation region 8 of catheter 6 via a lumen (not shown in FIG. 1) within catheter 6. Fluid is supplied to lumen from the source along a conductive fluid supply line 102 and a conduit 103, which is coupled to the inner catheter lumen at multi-lumen fitment 114. The source of conductive fluid (e.g., isotonic saline) may be an irrigant pump system (not shown) or a simple gravity-driven supply, such as an irrigant reservoir 100 positioned several feet above the level of the patient and tissue ablating region 8. A control valve 104 may be positioned at the interface of fluid supply line 102 and conduit 103 to allow manual control of the flow rate of electrically conductive fluid 30. Alternatively, a metering pump or flow regulator may be used to precisely control the flow rate of the conductive fluid.

System 2 further includes an aspiration or vacuum system (not shown) to aspirate liquids and gases from the target site, and syringes 106, 108 for inflating distal and proximal balloons 18, 40, respectively. By way of example, as the plunger of syringe 108 is depressed, fluid in the syringe chamber is displaced such that it flows through a conduit 107 and an internal lumen 57 within catheter 6(not shown in FIG. 1) to expand and inflate balloon 40. Likewise, syringe 106 is provided at the proximal end of guide wire 28 for inflating distal balloon 18, as shown by translation vectors 116, 118. Also, guidewire 28 can be advanced or retracted relative to tissue ablation region 8 of catheter 6 as shown by translation vectors 116, 118 such that, for each increment of relative displacement 116 at the proximal end of catheter 6, there is a corresponding displacement 118 of the hollow guidewire 28 relative to the tissue ablating region 8 of catheter 6.

Figure 2B:
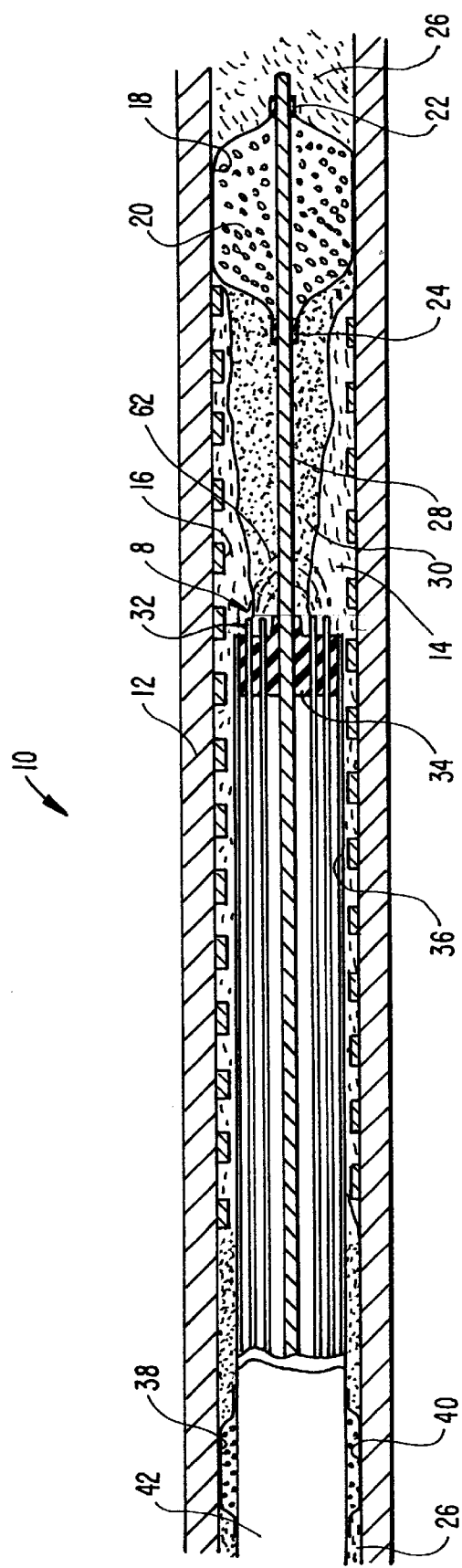
Figure 2C:
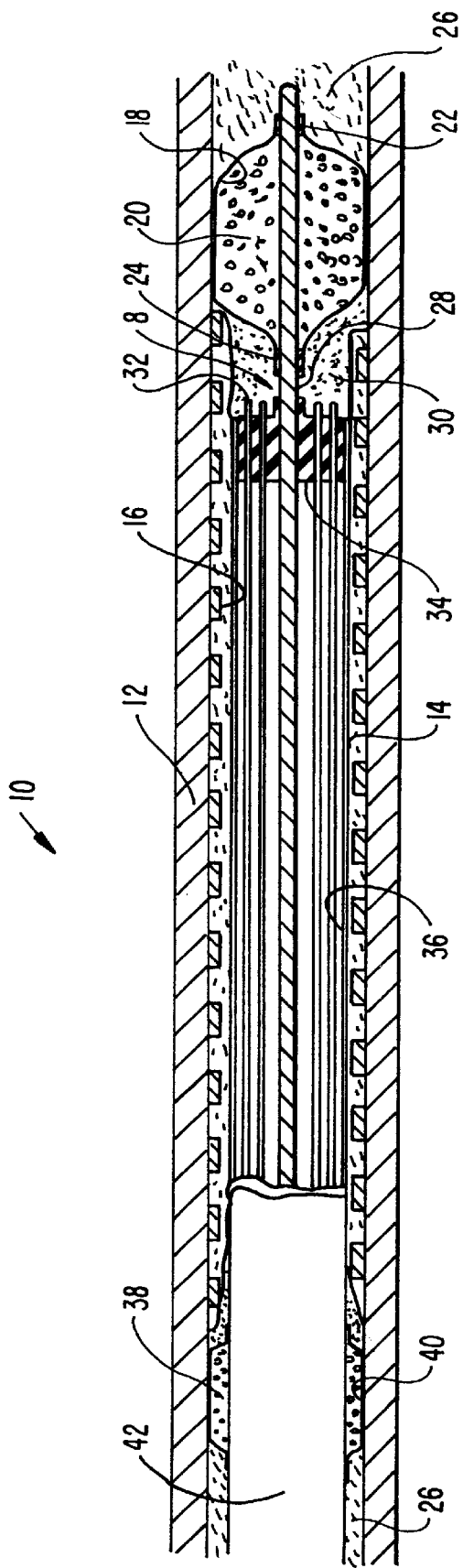

Referring now to FIGS. 2A–2C, one embodiment of the method and apparatus of the present invention will be described in detail. As shown, tissue ablating region 8 of catheter 6 progresses through occlusive media 14, such as atheromatous media or thrombus within a body lumen 10, e.g., a blood vessel. The principles of the present invention are also applicable to any body lumen which becomes partially or totally occluded. The present invention is particularly useful in a lumen containing a lumenal prosthesis, such as a stent 16, stent-graft or graft, which may be metallic, non-metallic or a non-metallic coated metallic structure. A particular advantage of the present invention is the confinement of current flow paths (not shown) between the return electrode (hollow guide wire 28 in the present example) and one or more active electrodes 32 to the vicinity of tissue ablating region 8. This confinement of current flow paths minimizes the undesired flow of current through portions or all of stent 16, which may otherwise induce non-specific tissue injury beyond the site of recanalization of the occluded lumen 10.

Referring to FIG. 2A, tissue ablating region 8 of catheter 6 is positioned proximal to the occlusive media 14 within lumen 10. The distal region of hollow guide wire 28 is positioned distal to the occlusive media 14 either before or after the initial positioning of tissue ablation region 8. Once hollow guide wire 28 is positioned as shown in FIG. 2A, proximal balloon 40 (not shown in FIG. 2A) is inflated to effect a seal between catheter shaft 42 and interior wall 12 of lumen 10 to minimize the flow of bodily fluid 26 (e.g., blood) from regions proximal to the tissue ablating region 8 of catheter 6. Electrically conductive and biologically compatible fluid 30 (e.g., isotonic saline) is delivered into lumen 10 for a sufficient period of time to displace naturally occurring bodily fluid 26 in the region between the tissue ablating region and the distal tip of guide wire 28. After the bodily fluid has been displaced, distal balloon 18 is inflated to effect a seal between balloon 18 and the interior wall 12 of lumen 10.

Once the target site is isolated from the rest of the vasculature, the supply of electrically conductive fluid 30 is continuously delivered to region 8 and balanced with the aspiration of fluid from the site of intended recanalization. The active electrode(s) 32 is (are) then energized by applying a high frequency voltage between active electrode(s) 32 and return electrode or guide wire 28. A high electric field is created at the surface of active electrode(s) 32 which causes the volumetric removal or ablation or target tissue in close proximity with active electrode(s) 32. The flow of electrical current between return electrode 28 and active electrode(s) 32 is shown by current flux lines 62 in FIG. 2B. As the occlusive media 14 is ablated, gaseous products are generated (not shown) which are entrained in the electrically conducting fluid 30 and removed through aspiration lumen 58 (not shown). The current flux lines 62 are generally confined to the central portion of tissue ablation region 8 because they generally flow inward towards return electrode 28 and because the occlusive media 14 generally shields the outer region of lumen (including stent 16) from flux lines 62. This minimizes undesirable interaction between the electrical current and stent 16.

Referring to FIG. 2C, this ablation procedure is continued until the desired length of the lumen containing occlusive media is recanalized. During the recanalization process, the products of ablation are confined between proximal balloon 40 and distal balloon 18 to minimize, for example, the injection of any non-condensable gaseous products of ablation into the blood stream which could otherwise lead to the formation of injurious or life-threatening emboli. Once the occlusive media 14 has been volumetrically removed (i.e., ablated), the energy application is suspended, the valve on the aspiration lumen is closed, control valve 104 is closed and balloons 18, 40 are deflated. The time period from the initial inflation of balloons 18, 40 to the deflation of these balloons is typically about 15–45 seconds, depending on the length and the extent of occlusion in the vessel. For longer occlusions, the above process may be repeated several times with intervals of no balloon inflation so that vital oxygen-bearing blood can be reperfused through the zone of intended recanalization to preserve the tissue distal to the recanalization zone.

Figure 3A:
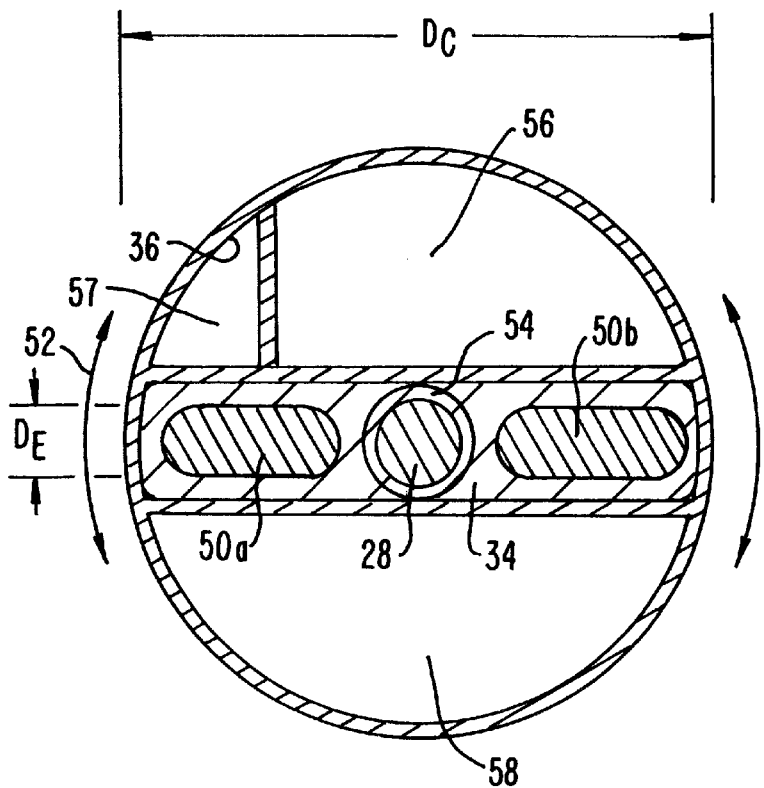
FIGS. 3A and 3B are transverse and longitudinal cross-sectional views, respectively, of a first embodiment of the distal portion of the catheter.
Figure 3B:
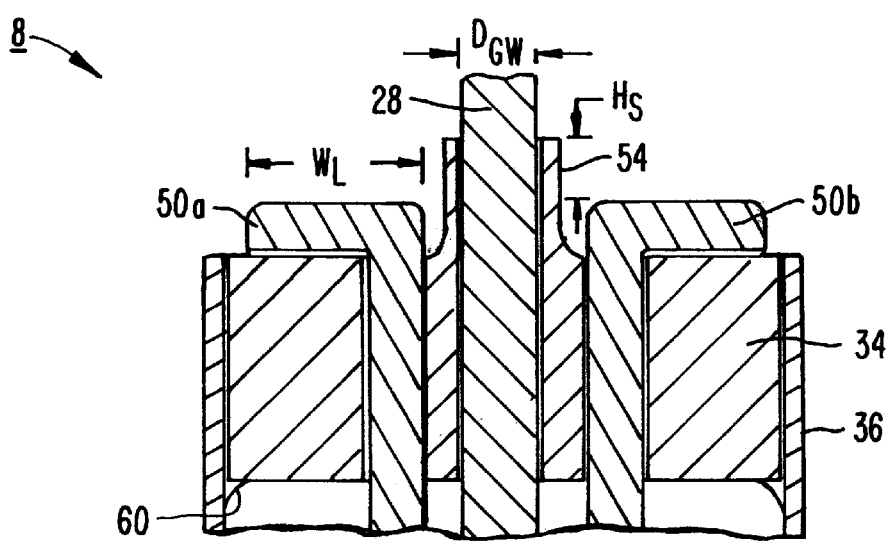

A first embodiment of tissue ablation region 8 of catheter 6 is shown in FIGS. 3A and 3B. As shown, two active electrodes 50a and 50b are secured within an electrically insulating support member 34. The electrodes 50a, 50b are preferably composed of a refractory, electrically conductive metal or alloy, such as platinum, titanium, tantalum, tungsten, stainless steel, gold, copper, nickel and the like. The support member 34 is secured to the distal end of catheter 6 with a biocompatible adhesive 60 between support member 34 and outer sleeve 36. An inorganic electrically insulating sleeve 54 preferably extends above the distal plane of active electrodes 50a, 50b by a distance $H_S$. A central lumen in support member 34 provides a passageway for guide wire 28 that permits axial displacement and rotation of tissue ablating region 8 relative to guide wire 28.

In an exemplary embodiment, the support member 34 will comprise an inorganic insulator, such as ceramic, glass, glass/ceramic or a high resistivity material, such as silicon or the like. An inorganic material is generally preferred for the construction of the support member 34 since organic or silicone based polymers are known to rapidly erode during sustained periods of the application of high voltages between electrodes 50 and the return electrode 28 during tissue ablation. However, for situations in which the total cumulative time of applied power is less than about one minute, organic or silicone based polymers may be used without significant erosion and loss of material of the support member 34 and, therefore, without significant reduction in ablation performance.

As shown in FIG. 3A, an irrigation lumen 56 and an aspiration lumen 58 are provided to inject electrically conducting fluid 30 and remove gaseous products of ablation 48 from the site of recanalization. An additional fluid lumen 57 provides fluid communication between inflation syringe 108 and proximal balloon 40. This fluid lumen 57 is filled with a sealant in those portions of the catheter distal to proximal balloon 40.

In use with the present invention, catheter 6 is rotated about 180 degrees clockwise and then about 180 degrees counter clockwise as the electrodes 50 are energized by generator 80 (FIG. 1) to effect ablation of the occlusive media. Using a reciprocating rotational motion combined with a small pressure to advance tissue ablation region 8 through the longitudinal length of the occlusive media 14 allow recanalization of the occluded vessel as described with reference to FIGS. 2A–2C. The cross-sectional shape of the active electrodes may be round wires as shown in FIG. 3B, or they may have shaped surfaces to enhance the electric field intensity at the distal surfaces of the active electrodes 50. Suitable electrode designs for use with the present invention may be found in co-pending, commonly assigned application Ser. No. 08/687,792, filed Jul. 19, 1996, the complete disclosure of which is incorporated herein by reference for all purposes.

Return electrode 28 comprises an electrically conducting material, usually metal, which is selected from the group consisting of stainless steel alloys, platinum or its alloys, titanium or its alloys, molybdenum or its alloys, and nickel or its alloys. The return electrode 28 may be composed of the same metal or alloy which forms the active electrodes 50 to minimize any potential for corrosion or the generation of electrochemical potentials due to the presence of dissimilar metals contained within an electrically conductive fluid 30, such as isotonic saline (discussed in greater detail below).

Figure 4A:
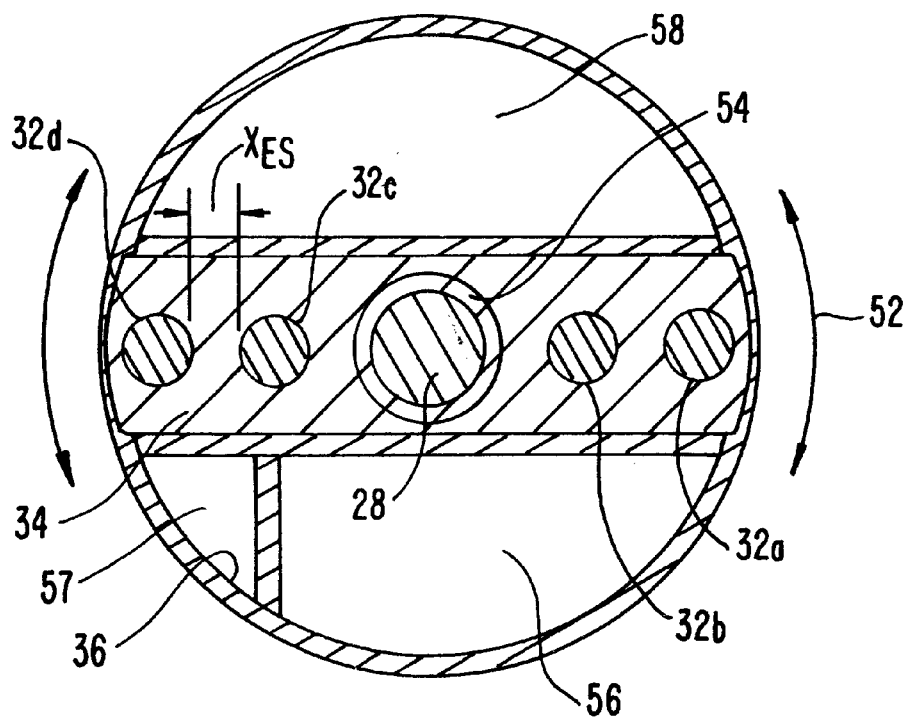
FIGS. 4A and 4B are transverse and longitudinal cross-sectional views, respectively, of a second embodiment of the distal portion of the catheter.
Figure 4B:
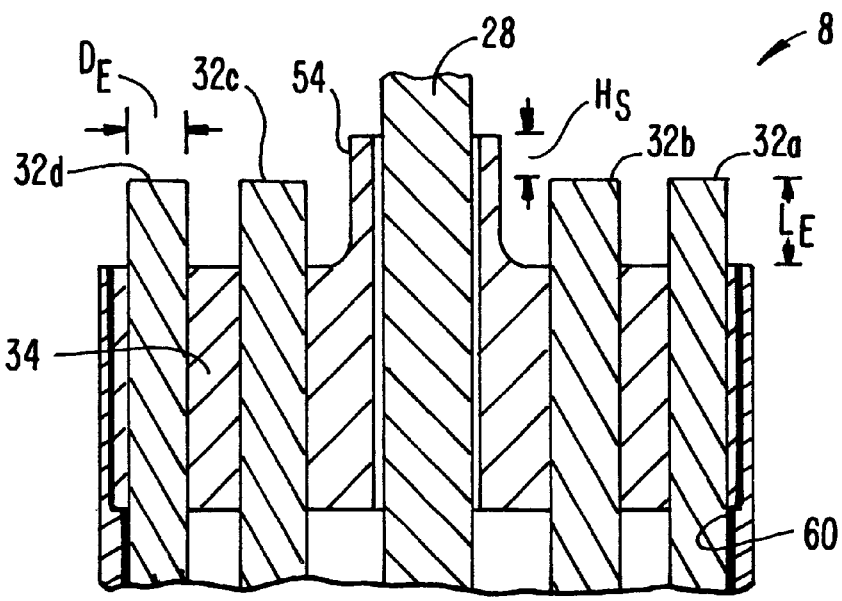

Referring now to FIGS. 4A and 4B, a second embodiment of tissue ablation region 8 of catheter 6 will now be described. In this embodiment, four active electrodes 32a, 32b, 32c, 32d are secured within an inorganic electrically insulating support member 34. Similar to the previous embodiment, support member 34 is secured to the distal end of catheter 6 with a biocompatible adhesive 60 between support member 34 and outer sleeve 36. An inorganic electrically insulating sleeve 54 preferably extends above the distal plane of active electrodes 50a, 50b by a distance $H_S$. A central lumen in support member 34 provides a passageway for guide wire 28 that permits axial displacement and rotation of tissue ablating region 8 relative to guide wire 28. As shown in FIG. 4A, an irrigation lumen 56 and an aspiration lumen 58 are provided to inject electrically conducting fluid 30 and remove gaseous products of ablation 48 from the site of recanalization. An additional fluid lumen 57 provides fluid communication between inflation syringe 108 and proximal balloon 40. This fluid lumen 57 is filled with a sealant in those portions of the catheter distal to proximal balloon 40.

In use, catheter 6 is rotated about 180 degrees clockwise and then about 180 degrees counter clockwise as the electrodes 32 are energized by generator 80 (FIG. 1) to effect ablation of the occlusive media. Using a reciprocating rotational motion combined with a small pressure to advance tissue ablation region 8 through the longitudinal length of the occlusive media 14 allow recanalization of the occluded vessel as described with reference to FIGS. 2A–2C. The cross-sectional shape of the active electrodes may be round wires as shown in FIG. 4B, or they may have shaped surfaces to enhance the electric field intensity at the distal surfaces of the active electrodes 32 as described co-pending, commonly assigned application Ser. No. 08/687,792, filed Jul. 19, 1996, the complete disclosure of which has previously been incorporated herein by reference.

Figure 5A:
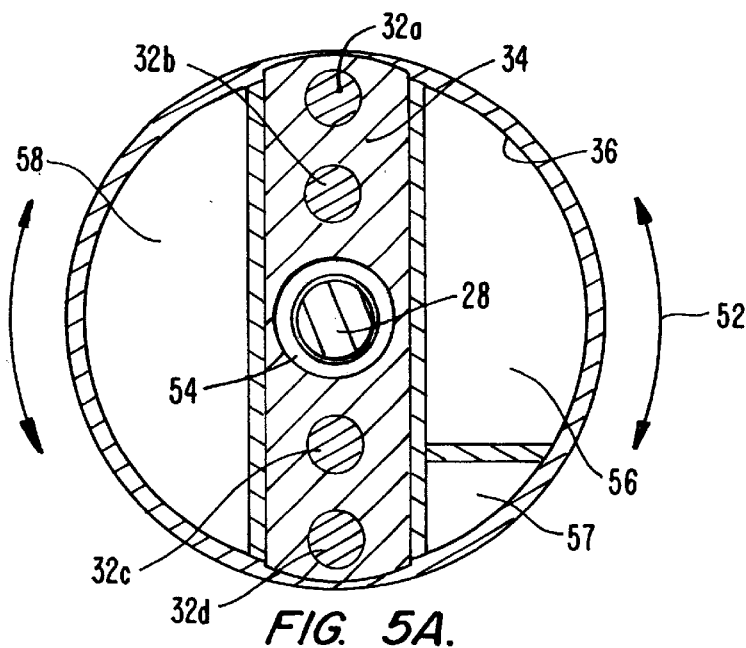
FIGS. 5A and 5B are transverse and longitudinal cross-sectional views, respectively, of the second embodiment of the distal portion of the catheter further illustrating the inflow of conductive liquid and aspiration of conductive liquid and gaseous products.
Figure 5B:
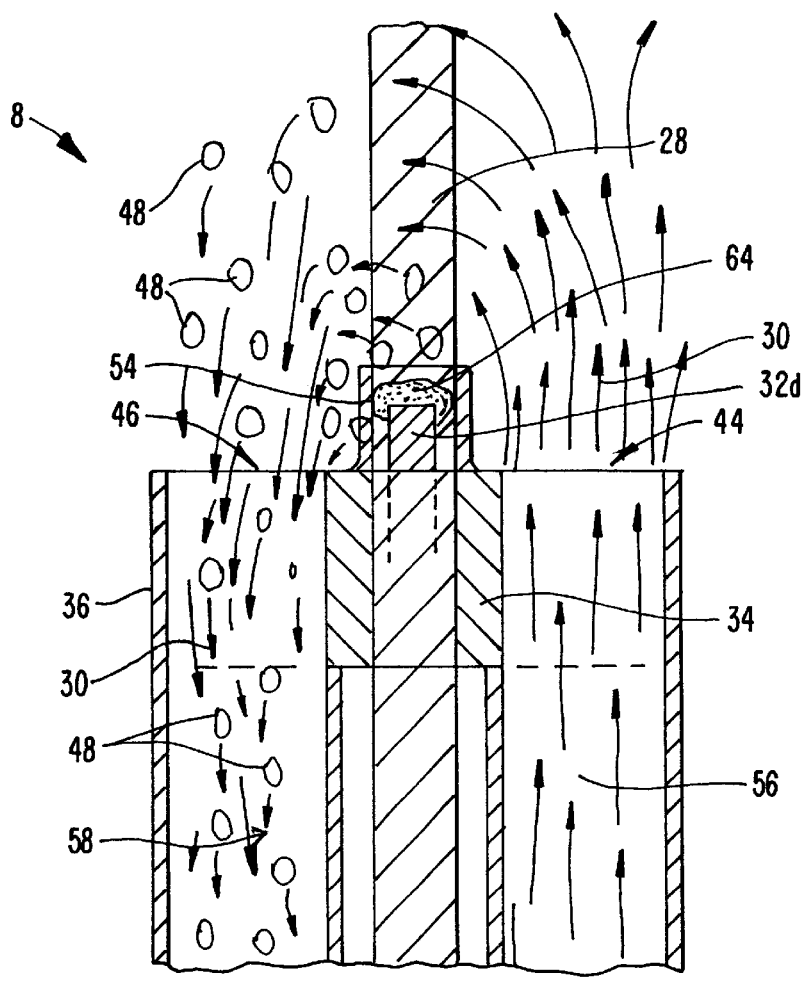

The second embodiment of FIGS. 4A and 4B is illustrated in greater detail in FIGS. 5A and 5B. As shown, electrically conductive fluid flows through irrigation lumen 56 of catheter 6 to and through irrigation port 44 and subsequently surrounds the target tissue site (i.e., occlusive media 14). When high frequency voltage is applied between the return electrode 28 and active electrodes 32, a vapor layer 64 forms at and around active electrodes 32 with concomitant volumetric removal (ablation) of the occlusive media 14. A more detailed description of this phenomena can be found in commonly assigned, co-pending application Ser. No. 08/561,958, filed on Nov. 22, 1995, the complete disclosure of which has previously been incorporated herein by reference. The occlusive media 14 is decomposes into gaseous products of ablation 48 which are entrained in electrically conducting fluid 30 and evacuated through aspiration port 46 and to the proximal end of catheter 6 via aspiration lumen 58.

Figure 6A:
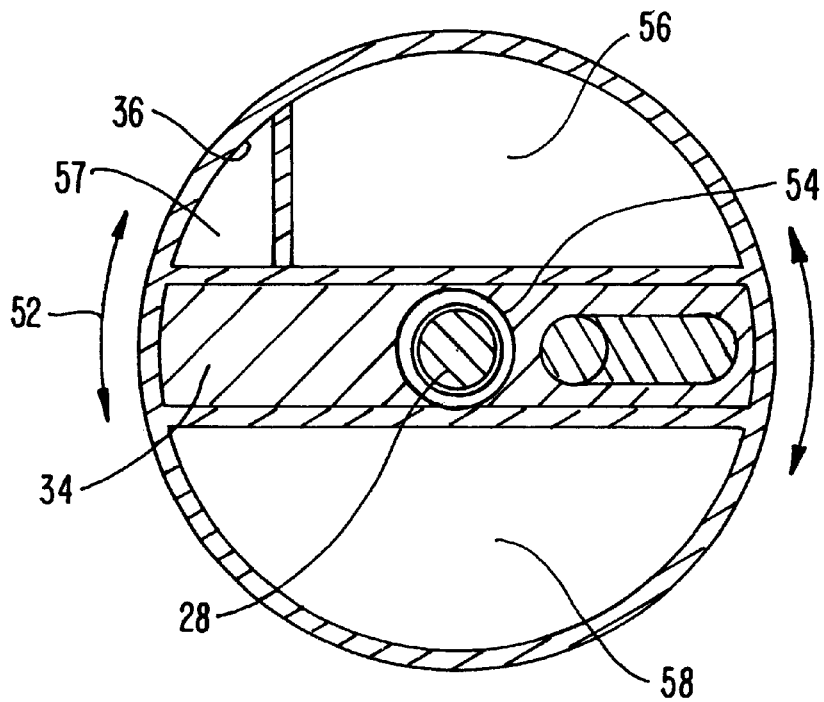
FIGS. 6A and 6B are transverse and longitudinal cross-sectional views, respectively, of a third embodiment of the distal portion of the catheter.
Figure 6B:
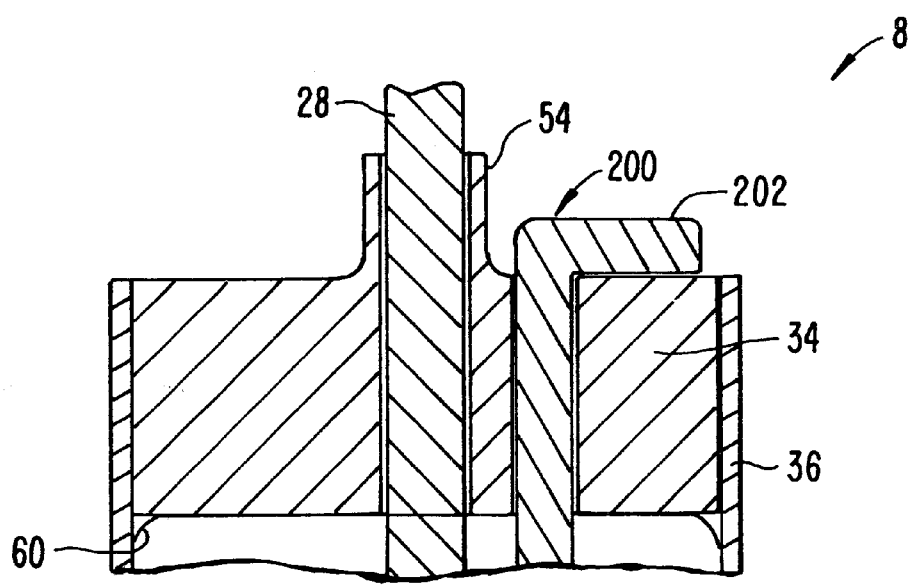

A third embodiment of tissue ablation region 8 is illustrated in FIGS. 6A and 6B. Many of the elements of this embodiment are the same as previous embodiments, and therefore will not be repeated. As shown, a single active electrode 200 is secured within support member 34. Active electrode 200 preferably has an L-shaped distal end so that a distal portion 202 of electrode 200 extends radially outward along the distal surface of support member 34. As before, electrode 200 is rotated in both directions, as the region 8 is advanced through the lumen to recanalize the lumen.

Figure 7A:
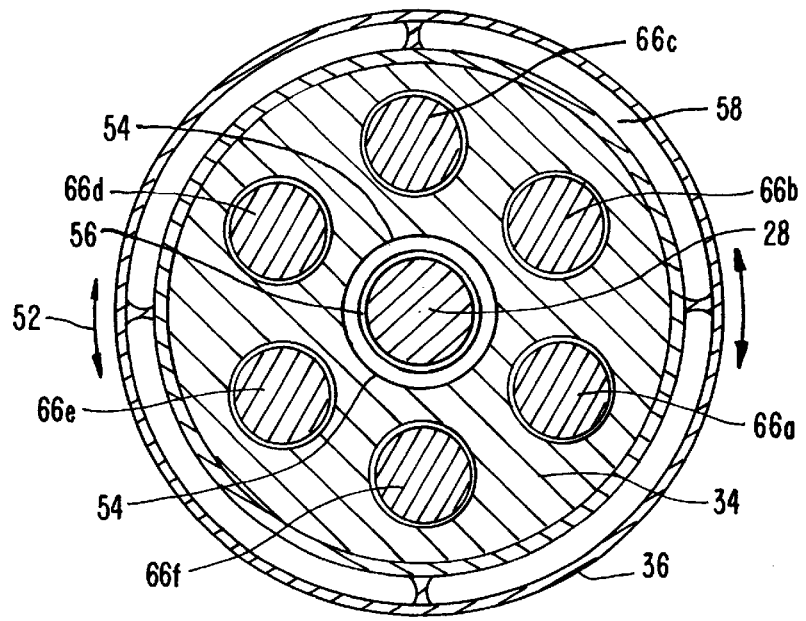
FIGS. 7A and 7B are transverse and longitudinal cross-sectional views, respectively, of a fourth embodiment of the distal portion of the catheter.
Figure 7B:
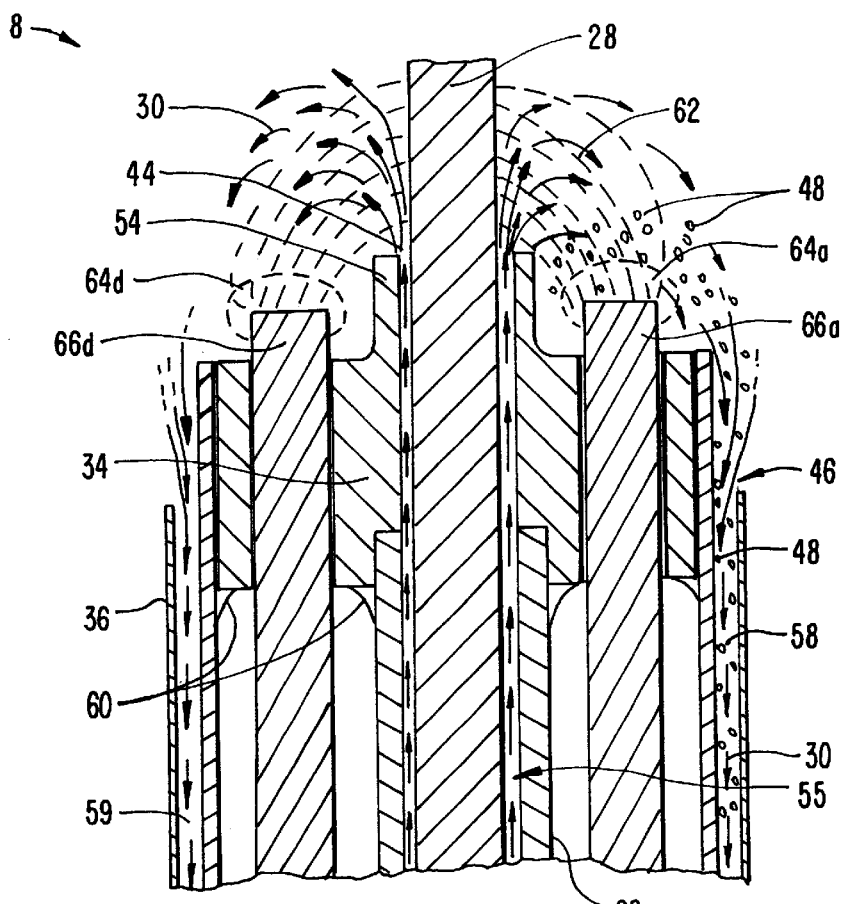

A fourth embodiment of tissue ablation region 8 is illustrated in FIGS. 7A and 7B. Many of the elements of this embodiment are the same as previous embodiments, and therefore will not be repeated. As shown, six active electrodes 66a–66f are secured within inorganic support member 34. An annular irrigation lumen 55 and an aspiration lumen 59 are provided to inject electrically conducting fluid 30 and remove gaseous products of ablation 48 from the site of recanalization. When high frequency voltage is applied between the return electrode 28 and active electrodes 66, a vapor layer 64 forms at and around active electrodes 66 with concomitant volumetric removal (ablation) of the occlusive media 14. For this embodiment and that shown in FIGS. 8A and 8B, rotation may be limited to +−30 degrees due to the greater number and circumferential distribution of active electrodes. The power or current supplied to each electrode may be individually controlled by active or passive mechanisms as previously described in commonly assigned, co-pending application Ser. No. 08/561,958, filed on Nov. 22, 1995. The occlusive media 14 is decomposed into gaseous products of ablation 48 which are entrained in electrically conducting fluid 30 and evacuated through aspiration port 46 and onto the proximal end of catheter 6 via aspiration lumen 59. As shown in FIG. 7b, the current flux lines 62 are confined to the central portions of tissue ablation region 8.

Figure 8A:
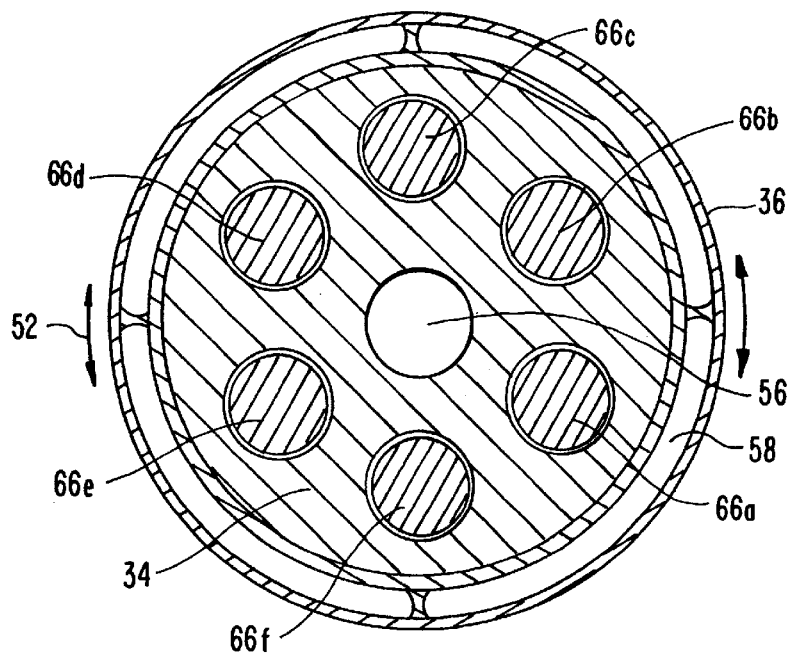
FIGS. 8A and 8B are transverse and longitudinal cross-sectional views, respectively, of a fifth embodiment of the distal portion of the catheter.
Figure 8B:
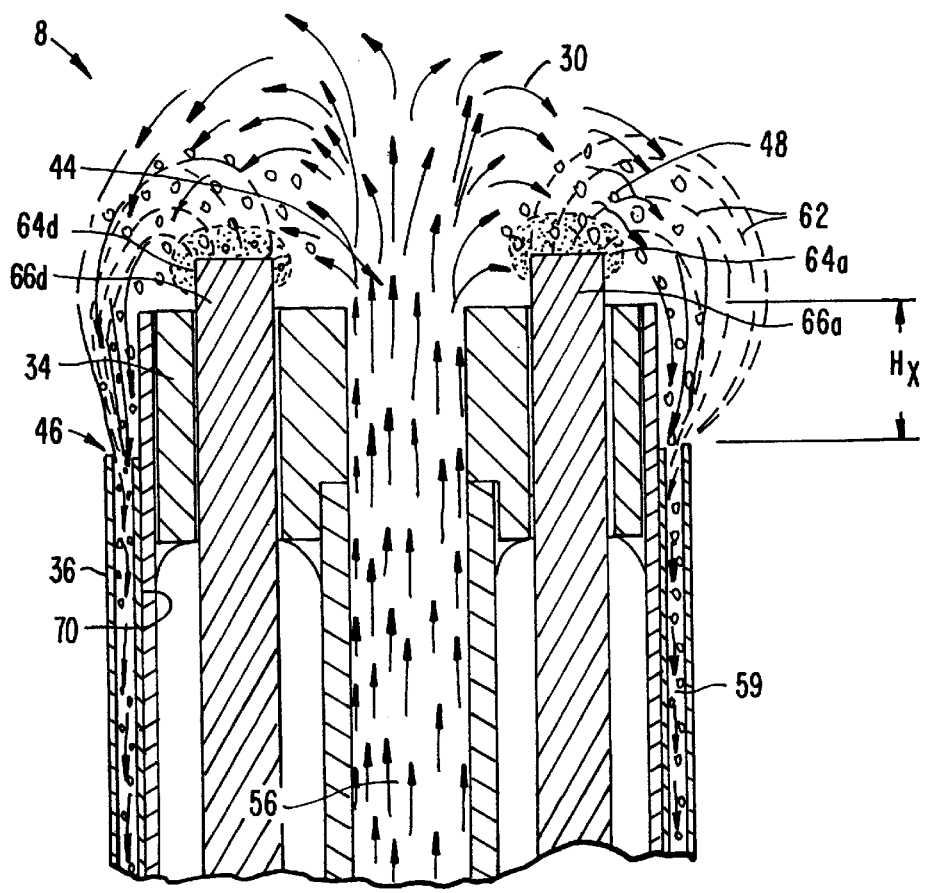

FIGS. 8A and 8B illustrate a fifth embodiment of the present invention. This embodiment is similar to the fourth embodiment in that six active electrodes 66a–66f are secured within inorganic support member 34. A return electrode 70 (e.g., metal sleeve) is positioned proximal to the active electrodes 66a–66f by a distance $H_X$. In this embodiment, current flux lines 62 travel proximally from the distal tips of electrodes 66 to the proximally spaced return electrode 70.

Figure 9A:
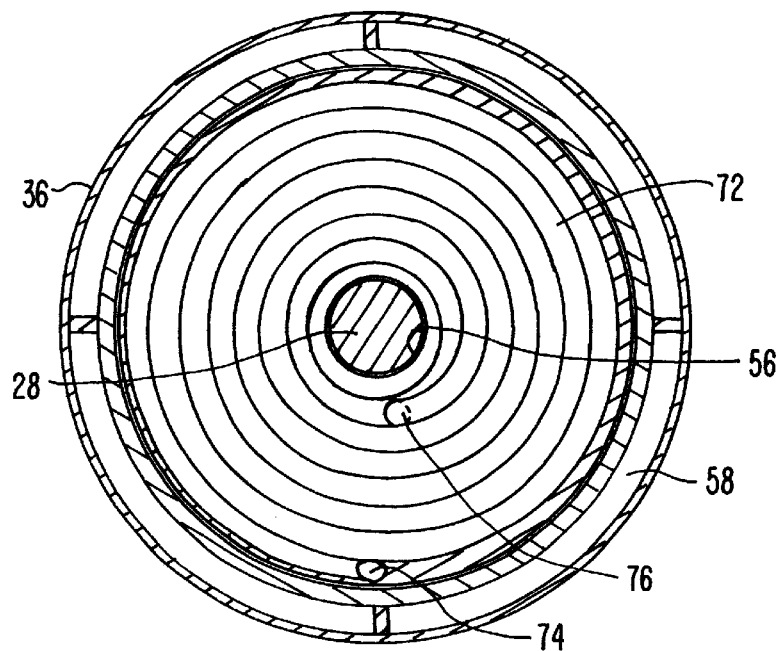
FIGS. 9A and 9B are transverse and longitudinal cross-sectional views, respectively, of a sixth embodiment of the distal portion of the catheter.
Figure 9B:
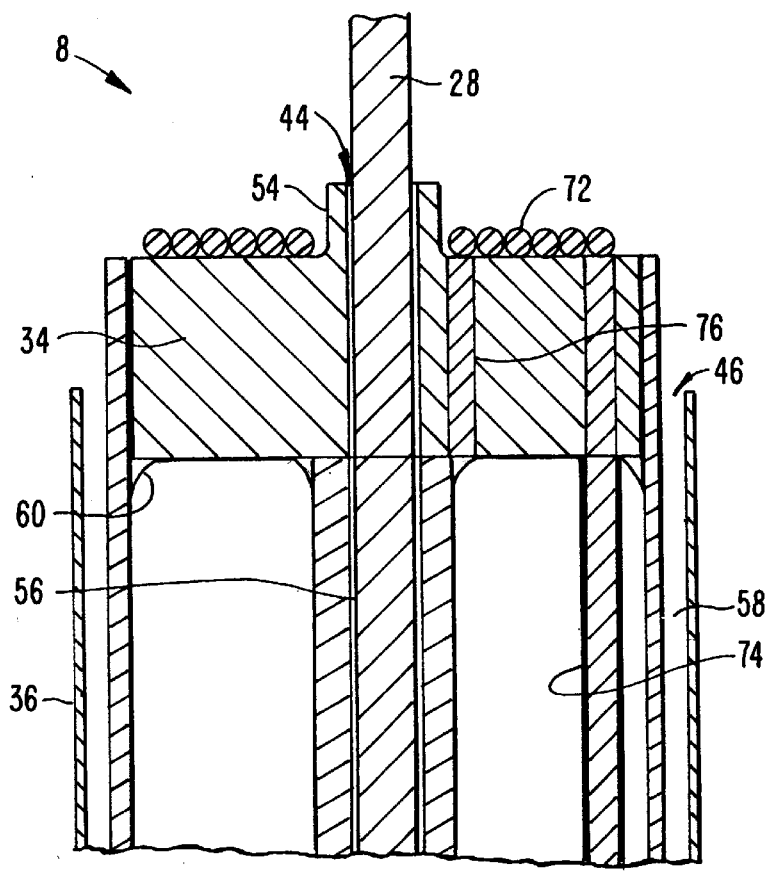

Referring to FIGS. 9A and 9B, a sixth embodiment of the invention will now be described. As shown, a single active electrode 72 is secured within inorganic support member 34. In this embodiment, active electrode 72 comprises a coiled wire having a plurality of concentric coils tightly and helically wrapped and secured on support member 34 (FIG. 9B). Preferably, the helical coil extends around return electrode 28 in concentric configuration, as shown in FIG. 9A.

Figure 10A:
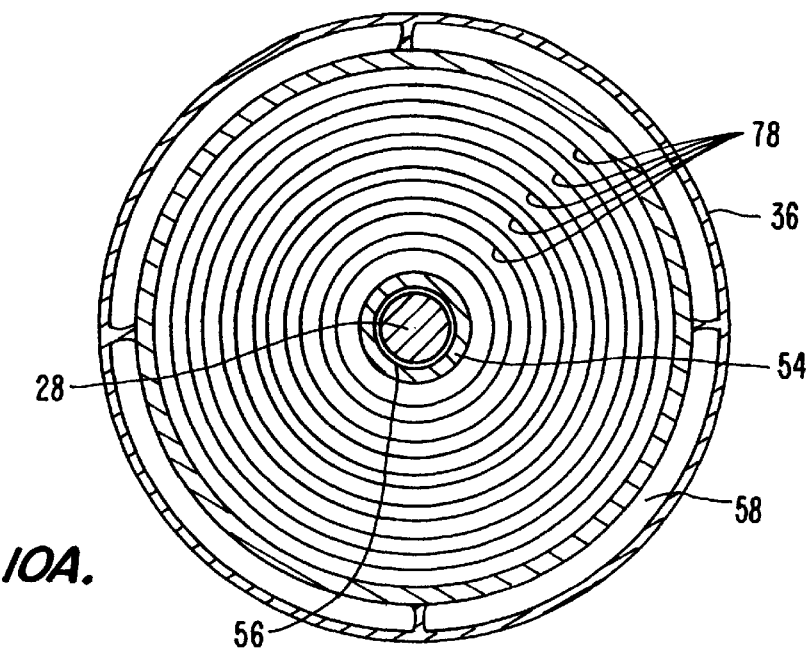
FIGS. 10A and 10B are transverse and longitudinal cross-sectional views, respectively, of a seventh embodiment of the distal portion of the catheter.
Figure 10B:
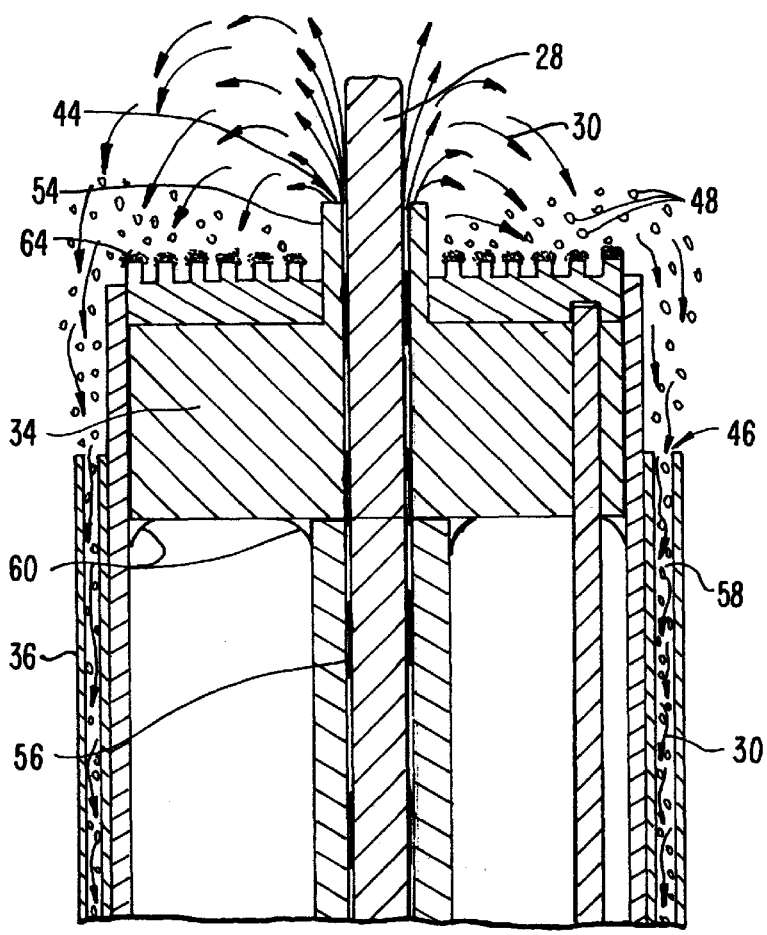

A seventh embodiment of the invention is shown in FIGS. 10A and 10B. This embodiment is similar to the sixth embodiment except that the single active electrode 73 defines a series of concentric machined grooves 75 to form concentric circular electrodes 78 surrounding return electrode 28. The distal edges of electrodes 78 generate regions of high electric field intensities when high frequency voltage is applied between return electrode 28 and concentric active electrodes 78. A vapor layer 64 forms at and around active electrodes 78 with concomitant volumetric removal (ablation) of the occlusive media. The embodiments of FIGS. 9 and 10 are usually advanced through the occlusive media without rotation.

As an alternative to the irrigation lumens shown above, the irrigant or electrically conductive fluid may be supplied through the lumen of tubular electrodes (not shown). This may be advantageous in ensuring that electrically conductive fluid is injected into close proximity to the site of tissue ablation/cutting. Further, the tubing can be filed to expose additional edges to enhance the tissue cutting effect.

During the percutaneous introduction and removal of catheter body 62, measures should be taken to prevent iatrogenic injury to the walls of the body lumen as the other tissues encountered along the pathway to the target site. In one embodiment, catheter 60 includes a compliant, atraumatic safety sheath (not shown) which extends over the working end of the catheter. In use, the sheath is advanced forward during introduction and removal of tissue ablation region 64. Once the target site has been accessed, the compliant, atraumatic safety sheath is retracted (e.g., a distance of 1.5 to 2.0 cm) exposing the electrode terminal(s). The safety sheath is preferably constructed using thin-walled plastic tubing selected to provide biocompatability, compliance and low friction during insertion and removal. A number of plastic materials are available for this purpose and include Teflon, polypropylene and polyvinyl chloride. The activation mechanism may be (1) the thin-walled plastic tubing moved relative to the catheter body at a location external to the patient's body or (2) a drive rod or wire (not shown) within the catheter body which actuates a short segment of the safety sheath (e.g., 4 to 8 cm) located at the distal end of the catheter body.

In another aspect of the invention, the catheter includes a radially expandable portion for allowing the diameter of an array of electrode terminals to be varied according to the diameter of the body lumen. In some instances, stents will not expand uniformly resulting in portions of the stent having smaller inner diameters. In other instances, vessel wall pressure may cause portions of the stent to spring back to its original shape or partially back to this shape so that the overall inner diameter of the stent varies in the axial direction. Accordingly, the present invention allows the diameter of the working end of the catheter to vary (either automatically in response to the body lumen or stent inner diameter, or through activation by the surgical team) to facilitate advancement through non-uniform stents or body lumens.

Figure 11:
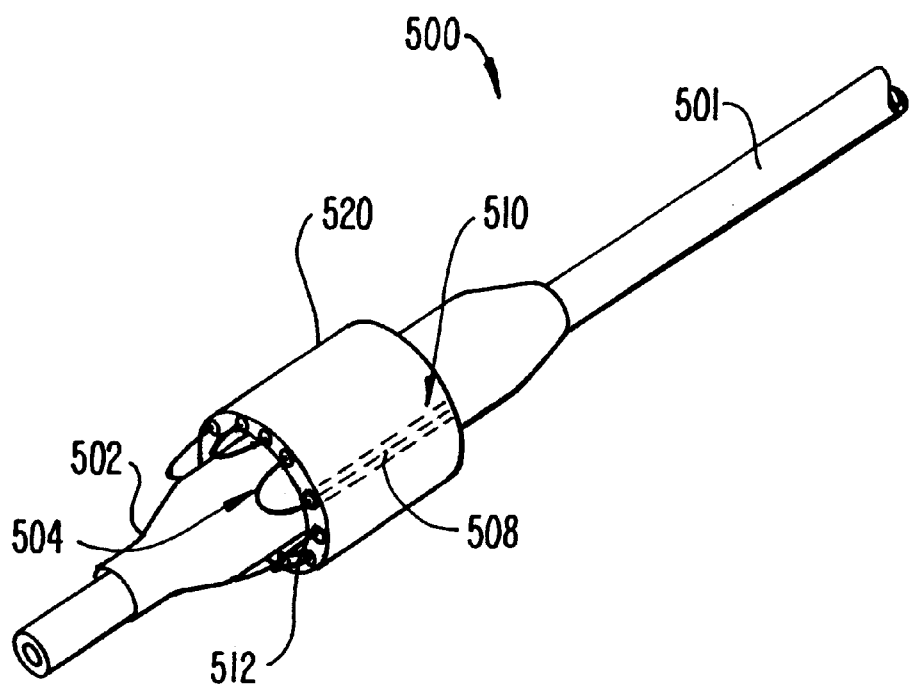
FIGS. 11 and 12 illustrate another embodiment of an electrosurgical catheter incorporating a radially expansible working end.
Figure 12:
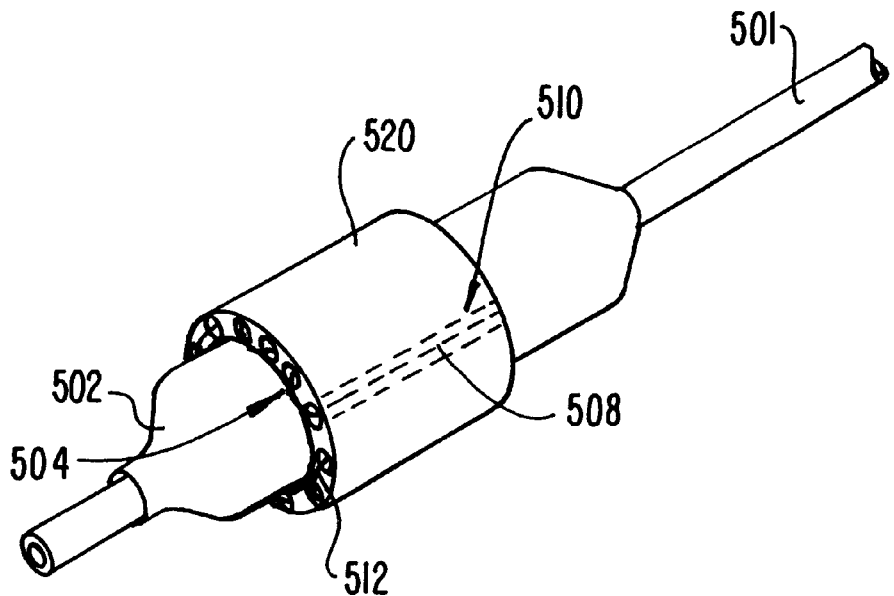

Referring now to FIGS. 11 and 12, a catheter 500 includes a catheter body 501 and a radially expansible working end portion 502 (e.g., a balloon or similar expansible member) supporting a plurality of electrode terminals 504 circumferentially spaced around the working end 502. Working end 502 preferably comprises an elastic material that will allow the working end 502 to expand up to at least 25 % of its original diameter, usually at least 100% of the original diameter, and often at least 200% of the original diameter (see FIG. 12). As shown, electrode terminals 504 are loops 512 formed by a pair of elongate wires 508 extending through tubular support members 510. This configuration provides the distal end of electrode terminals 504 with sufficient flexibility to expand outward (the loop straightens in the expanded configuration), as shown in FIG. 12. In this manner, the electrode terminals 504 can change their shape and dimensions as the expandable working end 502 expands or contracts. Of course, electrode terminals 504 may comprise a variety of other configurations. In addition, catheter 500 may include a single annular electrode terminal, as discussed above. Tubular support members 510 preferably comprise an inorganic material, such as ceramic or glass. Support members 510 are loosely coupled to each other with a flexible sheath 520. As the balloon 502 expands (FIG. 12), tubular support members 510 expand away from each other.

In the embodiment of FIGS. 11 and 12, the guidewire (not shown) functions as the return electrode. However, it will be understood that the return electrode may be positioned on the catheter proximal to the electrode terminals, and may be part of the expandable working end 502 of catheter 500. Alternatively, one or more of the electrode terminals 504 may serve as the return electrode(s) by applying the opposite polarity-to these electrode terminals 504.

Figure 12A:
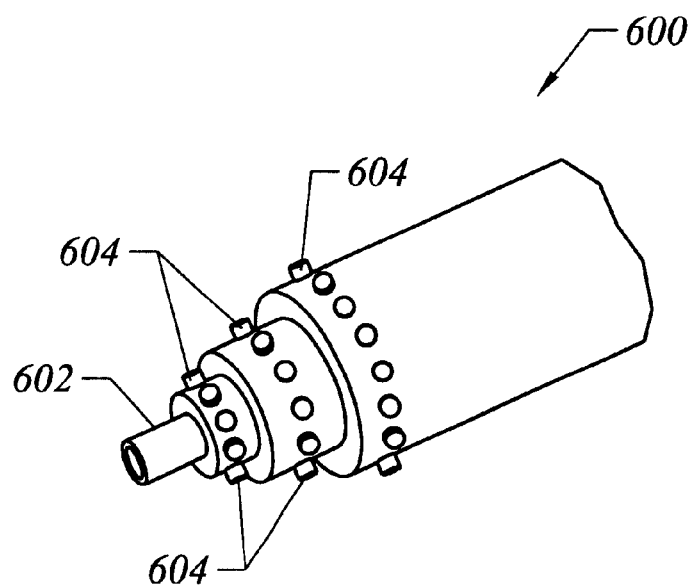
FIGS. 12A and 12B illustrate additional embodiments of electrosurgical catheters incorporating tapered working ends.
Figure 12B:
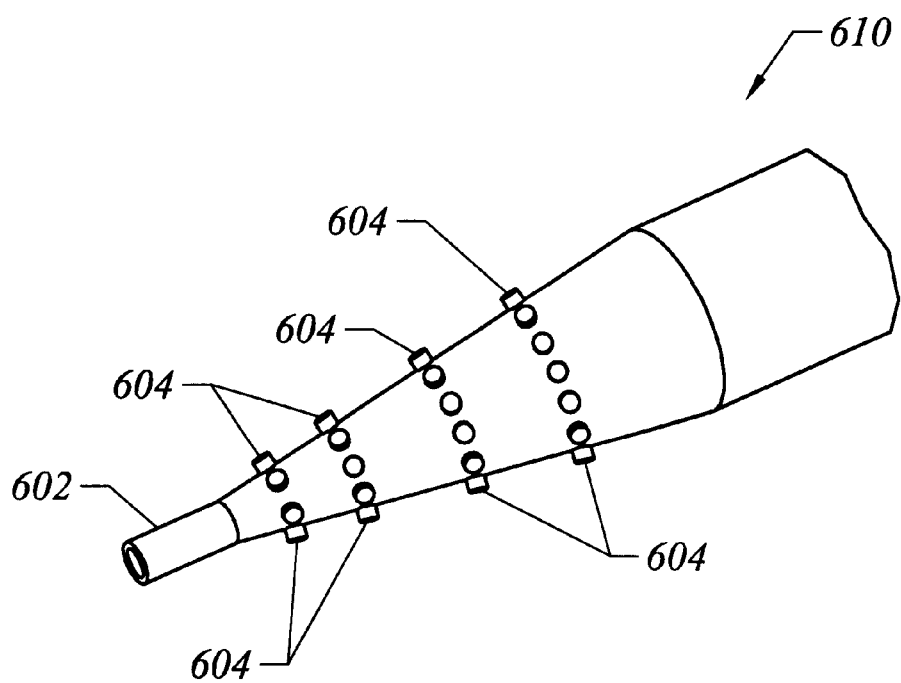

In other configurations, as shown in FIGS. 12A and 12B, the working end 602 of the catheter 600, 610 will taper in the distal direction (e.g., in a series of steps) so that the surgeon can advance the catheter through a severely occluded body lumen. The catheter 600, 610 may include a series of axially spaced electrode terminal(s) 604 that are electrically isolated from each other to allow for each set to be independently activated. By way of example, in a severely occluded body lumen, the surgeon may activate the distal set of electrode terminal(s) to remove the innermost occlusive media, advance these distal electrode terminal(s) 604 through the vacancy left by the removed occlusive media, and then activate a more proximal, and radially outward, set of electrode terminal(s) 604 to remove occlusive media radially outward from the initially removed media.

Figure 23:
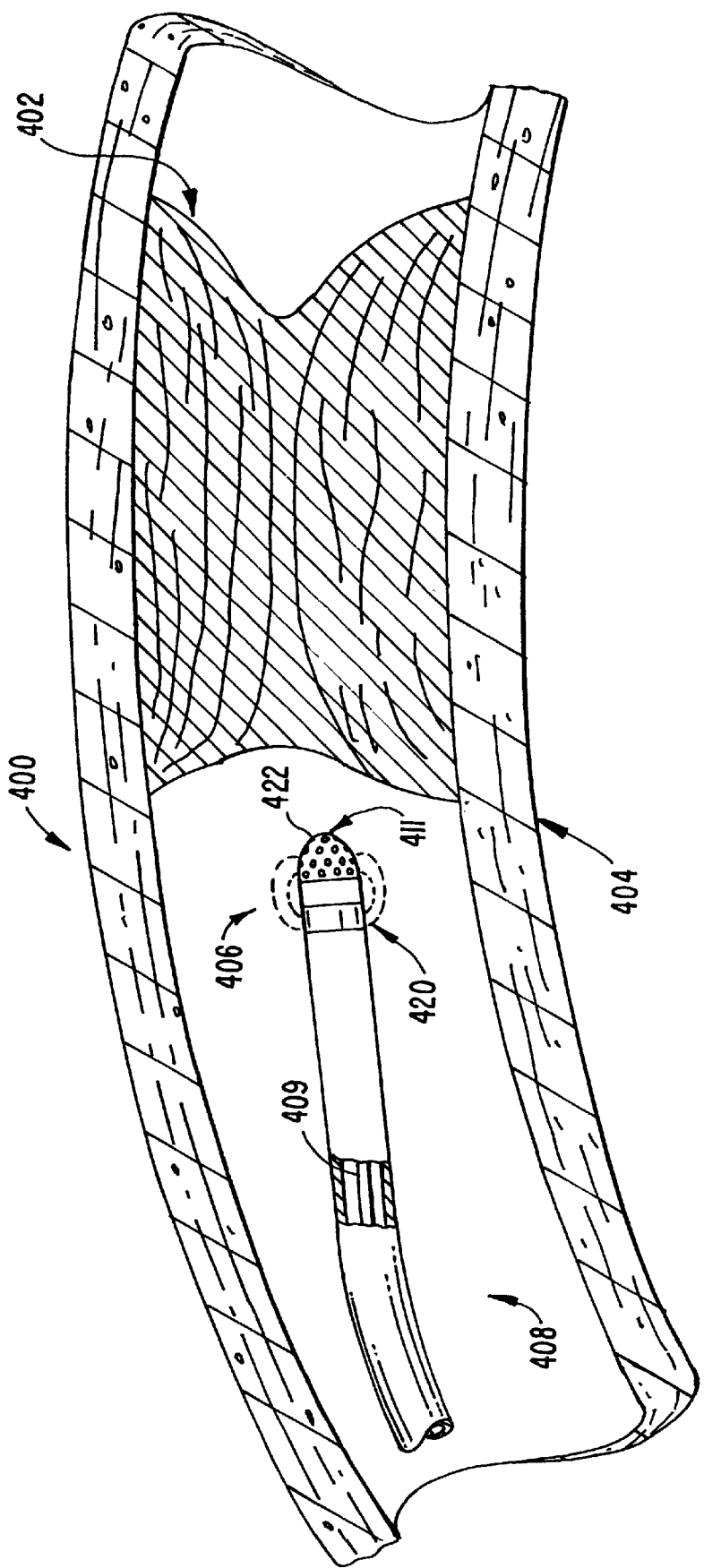
FIG. 23 illustrates a method of volumetrically removing media in a body passage having a total occlusion.

Referring now to FIG. 23, a method for recanalizing a severe occlusion 402 in a body passage 400 will be described. As shown, the occlusion 402 completely blocks the body passage, making it extremely difficult to recanalize with conventional catheter techniques. In these circumstances, it is necessary to at least partially recanalize (creating an opening through) the occlusion before conventional catheter procedures can begin. Conventional methods for recanalizing severe occlusions include hot-tipped catheters, laser catheters, and drill-tipped catheters. . These approaches rely on very aggressive treatment of the stenotic material, which can expose the blood vessel wall 404 to significant injury, for example, vessel perforation.

According to the present invention, the working end 406 of an electrosurgical catheter 408 is advanced through the body passage 400 to the site of recanalization. The catheter 408 may be advanced with a variety of techniques, such as a guidewire, steerable catheter and the like. Once the surgeon has reached the point of major blockage, electrically conductive fluid is delivered through one or more internal lumen(s) 409 within the catheter to the tissue. In some embodiments, the catheter may be configured to operate with a naturally occurring body fluid, e.g., blood, as the conductive medium. The fluid flows past the return electrode 420 to the electrode terminals 422 at the distal end of the catheter shaft. The rate of fluid flow is controlled with a valve (not shown) such that the zone between the occlusion and electrode terminal(s) 422 is constantly immersed in the fluid. The power supply 28 is then turned on and adjusted such that a high frequency voltage difference is applied between electrode terminals 422 and return electrode 420. The electrically conductive fluid provides the conduction path (see current flux lines) between electrode terminals 422 and the return electrode 420.

Figure 24A:
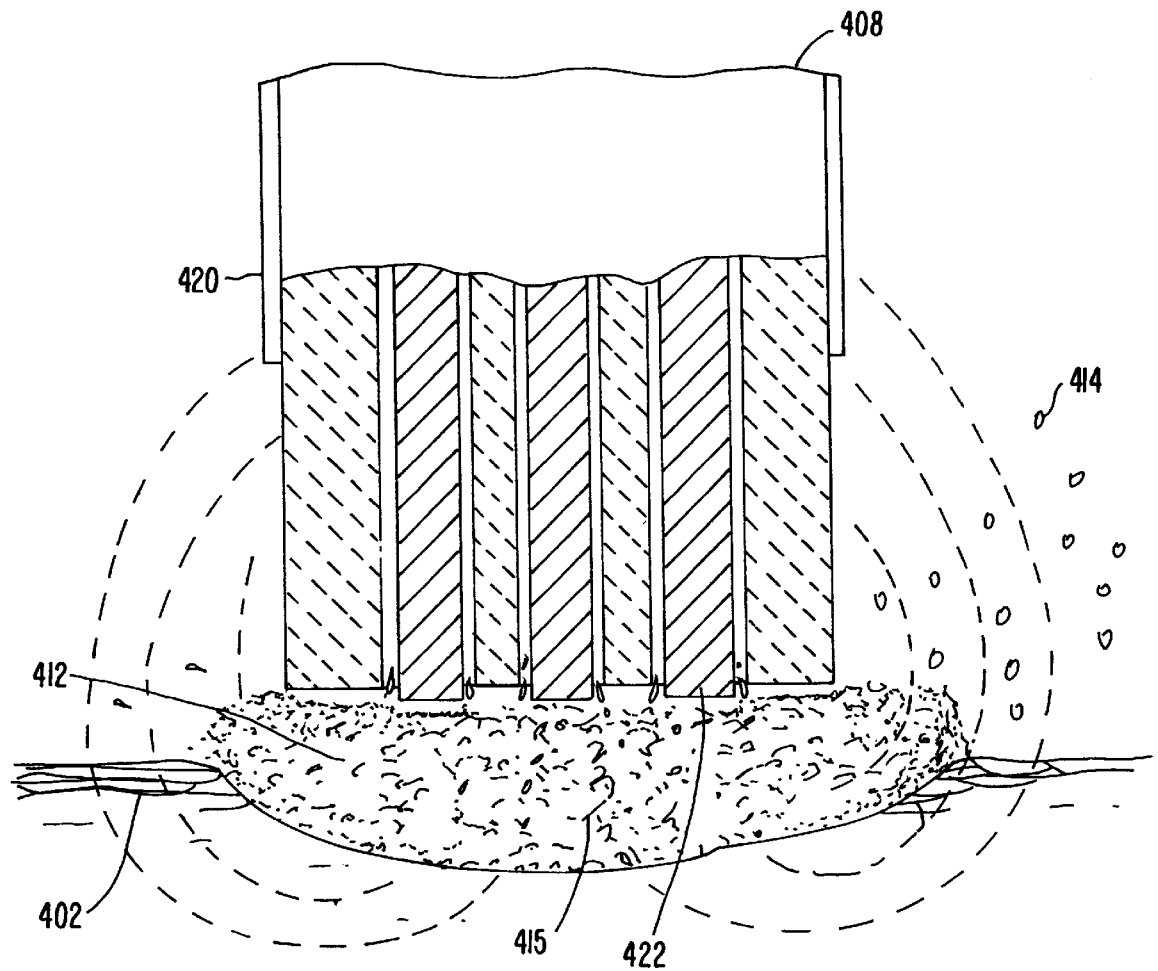
FIGS. 24A and 24B illustrate the volumetric removal of occlusive media in more detail.
Figure 24B:
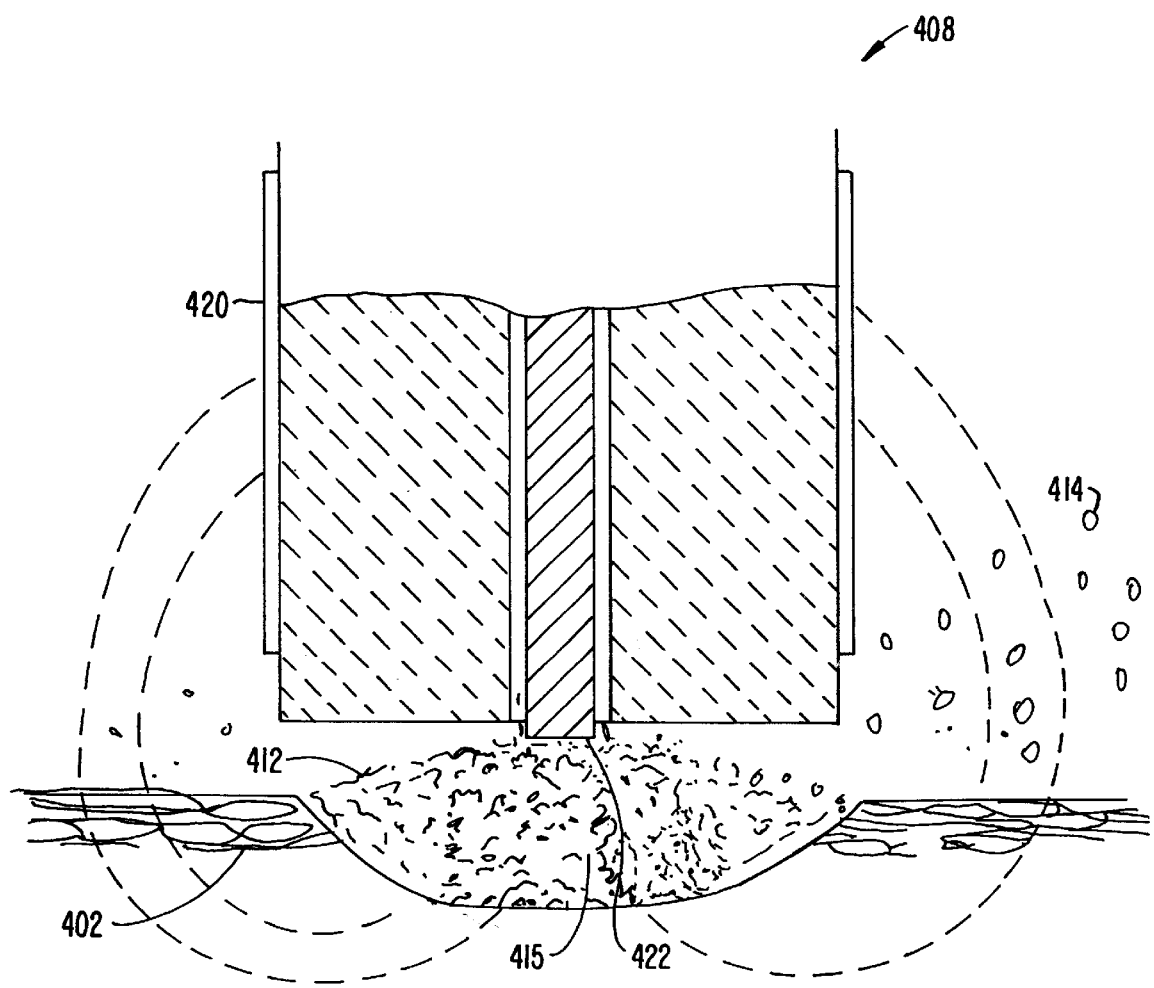

FIGS. 24A and 24B illustrate the volumetric removal of occlusive media in more detail As shown, the high frequency voltage is sufficient to convert the electrically conductive fluid (not shown) between the occlusion 402 and electrode terminal(s) 422 into an ionized vapor layer 412 or plasma. As a result of the applied voltage difference between electrode terminal(s) 422 and the occlusive media 402 (i.e., the voltage gradient across the plasma layer 412), charged particles 415 in the plasma (viz., electrons) are accelerated towards the occlusion. At sufficiently high voltage differences, these charged particles 415 gain sufficient energy to cause dissociation of the molecular bonds within tissue structures. This molecular dissociation is accompanied by the volumetric removal (i.e., ablative sublimation) of tissue and the production of low molecular weight gases 414, such as oxygen, nitrogen, carbon dioxide, hydrogen and methane. The short range of the accelerated charged particles 415 within the tissue confines the molecular dissociation process to the surface layer to minimize damage and necrosis to the surrounding vessel wall 404. During the process, the gases 414 may be aspirated through catheter 408. In addition, excess electrically conductive fluid, and other fluids (e.g., blood) may be aspirated from the target site to facilitate the surgeon's view.

What is claimed is:

1. A method for recanalizing a body lumen having occlusive media therein, the method comprising:

providing a catheter shaft with distal and proximal end portions and an electrode terminal at the distal end portion;

advancing the catheter shaft through the body lumen to position the electrode terminal into at least close proximity with the occlusive media;

applying a high frequency voltage to the electrode terminal, wherein the high frequency voltage is sufficient to recanalize the body lumen; and varying an outer diameter of the distal end portion of the catheter shaft to correspond with variations in the inner diameter of the body lumen.

2. The method of claim 1 wherein the varying step comprises providing the catheter shaft with a tapered distal end portion.

3. The method of claim 2 wherein the tapered distal end portion is continuous, the shaft comprising a plurality of electrically isolated electrode terminals spaced axially along the distal end portion.

4. The method of claim 2 wherein the tapered distal end portion includes discontinuities to form a series of segments each having a different outer diameter, wherein the shaft comprises at least one electrically isolated electrode terminal on each of the segments.

5. The method of claim 1 wherein the varying step comprises changing the diameter of the distal end portion of the catheter shaft during or after the applying step.

6. A catheter for maintaining patency in a body passage, the catheter comprising:

a catheter body having a distal end portion and a proximal end portion;

an electrode terminal positioned on the distal end portion of the catheter body, the electrode terminal comprising a wire loop; and a connector extending through the catheter body for coupling the electrode terminal to a source of high frequency electrical energy, wherein the distal end portion of the catheter body has a variable outer diameter to correspond with variations in an inner diameter of the body passage.

7. The catheter of claim 6 wherein the distel end portion of the catheter body is movable between first and second configurations having first and second diameters, respectively.

8. The catheter of claim 7 further comprising an actuator for moving the distal end portion of the catheter body between the first and second configurations.

9. A catheter system for maintaining patency in a body lumen, the catheter system comprising:
   a catheter body having distal and proximal end portions, the distal end portion having a variable diameter;
   an electrode terminal positioned on the distal end portion of the catheter body, the electrode terminal adapted for volumetrically removing an occlusive media;
   a return electrode positioned on the catheter body;
   a high frequency power supply coupled to the electrode terminal for applying sufficient high frequency voltage to the electrode terminal to volumetrically remove the occlusive media within the body lumen; and
   one or more connectors extending through the catheter body for coupling the electrode terminal and the return electrode to the high frequency power supply.

10. The catheter system of claim 9 wherein the return electrode is positioned on the distal end portion of the catheter body radially inward from the electrode terminal.

11. The catheter system of claim 9 wherein the return electrode is a guidewire extending through an internal lumen of the catheter body and through a distal opening in the catheter body, the electrode terminal being disposed on a distal tip of the catheter body radially outward from the guidewire.

12. The catheter system of claim 9 further comprising:
   a source of electrically conducting fluid; and
   an internal lumen within the catheter body, the internal lumen coupled to the electrically conducting fluid source for delivering electrically conducting fluid between the return electrode and the electrode terminal.

13. The catheter system of claim 9, wherein the distal end portion of the cotheter body tapered, the catheter body comprising a plurality of electrically isolated electrode terminals spaced axially along the distal end portion.

14. The catheter system of claim 9 wherein the distal end portion of the catheter body comprises a series of segments each having a different outer diameter, wherein the catheter body comprises at least one electrically isolated electrode terminal on each of the segments.

15. The catheter system of claim 9 wherein the distal end portion of the catheter body comprises an expansible member movable between first and second configurations having first and second diameters, respectively.

16. The catheter system of claim 15 further comprising an actuator for moving the distal end portion of the catheter body between the first and second configurations.

17. The catheter system of claim 15 further comprising a plurality of tubular support members circumferentially spaced around the expansible member, wherein the electrode terminal comprises a plurality of electrode terminals, and one of the plurality of electrode terminals extending from a distal end of each of the tubular support members.

18. The catheter system of claim 17 wherein each of the plurality of tubular support members comprise an inorganic material.

19. The catheter system of claim 17 wherein each of the plurality of electrode terminals comprises a wire loop formed by a pair of wires that come together at a point distal of the plurality of tubular support members, wherein each wire extends through one of the plurality of tubular support members.

20. A method for recanalizing a body lumen having occlusive media therein, the method comprising:
   a) advancing a catheter through the body lumen towards the occlusive media, wherein the catheter includes a catheter body having a distal end portion and a proximal end portion, the distal end portion having at least one electrode terminal and a return electrode;
   b) positioning the at least one electrode terminal in at least close proximity to the occlusive media, wherein the at least one electrode terminal is positioned within an electrically conductive fluid, such that the electrically conductive fluid provides a current flow path between the at least one electrode terminal and the return electrode; and
   c) applying a high frequency voltage between the at least one electrode terminal and the return electrode, the high frequency voltage sufficient to volumetrically remove the occlusive media, whereby the body lumen is recanalized.

21. The method of claim 20, further comprising expanding the distal end portion of the catheter body.

22. The method of claim 21, further comprising varying an outer diameter of the distal end portion of the catheter body to accommodate variations in inner diameter of the body lumen.

23. The method of claim 20, wherein the electrically conductive fluid comprises blood or saline.

24. The method of claim 20, further comprising:
   d) prior to or during said step c), delivering an electrically conductive fluid to the distal end portion.

25. The method of claim 20, further comprising prior to said step c), fluidly isolating the occlusive media.

26. The method of claim 25, wherein the catheter further includes a distal balloon and a proximal balloon, and said step e) comprises:
   f) positioning the proximal balloon at a location proximal to the occlusive media, wherein the at least one electrode terminal is located distal to the proximal balloon;
   g) inflating the proximal balloon to prevent fluid flow between the catheter body and an inner wall of the body lumen;
   h) positioning the distal balloon at a location distal to the occlusive media; and
   i) inflating the distal balloon to prevent fluid flow through the body lumen at the location of the distal balloon.

27. The method of claim 26, further comprising:
   j) prior to said step i), delivering an electrically conductive fluid within the body lumen to a location distal to the proximal balloon, whereby naturally occurring bodily fluid is displaced from the body lumen at a location between the proximal balloon and the distal balloon.

28. The method of claim 27, wherein the electrically conductive fluid comprises isotonic saline.

29. The method of claim 20, further comprising during or after said step c), aspirating ablation by-products from within the body lumen in the vicinity of the occlusive media.

30. The method of claim 20, wherein the at least one electrode terminal comprises an electrode array.

31. The method of claim 30, further comprising expanding the distal end portion of the catheter body, and wherein the electrode array undergoes a change in diameter as the distal end portion expands.

32. The method of claim 31, wherein the electrode array comprises a plurality of electrode terminals.

33. The method of claim 32, wherein each of the plurality of electrode terminals undergoes a change in shape when the distal end portion undergoes a change in diameter.

34. The method of claim 32, wherein the plurality of electrode terminals are circumferentially arranged on the distal end portion.

35. The method of claim 32, wherein each of the plurality of electrode terminals comprises a wire loop.

36. The method of claim 31, wherein said step b) comprises positioning the at least one electrode terminal in an orientation substantially parallel to the longitudinal axis of the body lumen.

37. The method of claim 20, wherein the return electrode is located proximal to the at least one electrode terminal.

38. A bipolar electrosurgical catheter, comprising:

a catheter body having a distal end portion and a proximal end portion; and a plurality of electrode terminals disposed on the distal end portion, each of the plurality of electrode terminals aligned substantially parallel to the longitudinal axis of the distal end portion, wherein the distal end portion is expandable to provide a variable diameter electrode array.

39. The catheter of claim 38, wherein the distal end portion is expandable by from about 25% to 200% of its original diameter.

40. The catheter of claim 38, wherein the variable diameter electrode array is adapted to accommodate variations in an inner diameter of a body lumen.

41. The catheter of claim 38, wherein the plurality of electrode terminals of the electrode array are circumferentially arranged on the distal end portion.

42. The catheter of claim 38, wherein the electrode array is annular, and each of the plurality of electrode terminals is located equidistant from the catheter body.

43. The catheter of claim 38, wherein each of the plurality of electrode terminals comprises a wire loop.

44. The catheter of claim 38, wherein the plurality of electrode terminals are supported by a corresponding plurality of tubular support members.

45. The catheter of claim 44, wherein the plurality of tubular support members are coupled to each other by a flexible sheath.

46. The catheter of claim 38, further comprising at least one inflatable balloon, the at least one inflatable balloon adapted for inflation within a body lumen.

47. The catheter of claim 38, further comprising a proximal balloon and a distal balloon.

48. The catheter of claim 47, wherein the catheter further includes a hollow guidewire, and wherein the distal balloon is inflated via the guidewire.

49. The catheter of claim 38, further including a return electrode.

50. The catheter of claim 49, wherein the return electrode is located radially inward from the electrode array.

51. The catheter of claim 49, wherein the return electrode comprises a guidewire.

* * * * *